United States Patent [19]
Conzemius et al.

[11] Patent Number: 6,162,253
[45] Date of Patent: Dec. 19, 2000

[54] TOTAL ELBOW ARTHROPLASTY SYSTEM

[75] Inventors: Michael G. Conzemius; Rhonda L. Aper, both of Ames, Iowa

[73] Assignee: Iowa State University Research Foundation, Inc., Ames, Iowa

[21] Appl. No.: 09/207,689

[22] Filed: Dec. 9, 1998

Related U.S. Application Data

[60] Provisional application No. 60/071,885, Dec. 31, 1997.

[51] Int. Cl.$^7$ ........................................................ A61F 2/38
[52] U.S. Cl. ................................... 623/20.11; 623/18.11
[58] Field of Search .................................. 623/20, 20.11, 623/20.12, 20.13, 20.14, 20.21

[56] References Cited

U.S. PATENT DOCUMENTS

| | | | |
|---|---|---|---|
| 3,656,186 | 4/1972 | Dee | 623/20.12 |
| 3,708,805 | 1/1973 | Scales et al. | 623/20.12 |
| 3,816,854 | 6/1974 | Schlein | 623/20.12 |
| 4,079,469 | 3/1978 | Wadsworth | 623/20.12 |
| 4,085,466 | 4/1978 | Goodfellow et al. . | |
| 4,219,893 | 9/1980 | Noiles . | |
| 4,224,695 | 9/1980 | Grundei et al. | 623/20.12 |
| 4,364,389 | 12/1982 | Keller | 606/86 |
| 4,378,607 | 4/1983 | Wadsworth . | |
| 4,383,337 | 5/1983 | Volz et al. | 623/20.12 |
| 4,677,973 | 7/1987 | Slocum | 128/92 |
| 4,686,978 | 8/1987 | Wadsworth | 606/84 |
| 4,822,364 | 4/1989 | Inglis et al. . | |
| 4,834,081 | 5/1989 | Van Zile | 606/99 |
| 4,950,298 | 8/1990 | Gustilo et al. . | |
| 5,282,868 | 2/1994 | Bahler . | |
| 5,304,180 | 4/1994 | Slocum | 606/69 |
| 5,318,571 | 6/1994 | Benson . | |
| 5,330,533 | 7/1994 | Walker . | |
| 5,376,121 | 12/1994 | Huene et al. | 623/20 |
| 5,578,038 | 11/1996 | Slocum | 606/87 |
| 5,603,717 | 2/1997 | Benson . | |
| 5,683,468 | 11/1997 | Pappas . | |
| 5,782,923 | 7/1998 | Engelbrecht et al. | 623/20 |
| 5,788,705 | 8/1998 | Huddleston et al. . | |
| 5,800,558 | 9/1998 | LaHaise, Sr. . | |
| 5,879,389 | 3/1999 | Koshino | 623/20 |
| 5,879,395 | 3/1999 | Tornier | 623/20 |
| 6,027,534 | 2/2000 | Wack et al. | 623/20 |

OTHER PUBLICATIONS

Sixth Annual ACVS Symposium Proceedings Small Animal, *Development of Elbow Arthroplasty (Canine) Clinical Trials*, Ralph H. Lewis, DVM; Diagnostic Osteonecrosis Center & Research Foundation, Lakeport, California; p. 110 (1996).

M.J. Kraay, et al., *Primary Semiconstrained Total Elbow Arthroplasty—Survival Analysis of 113 Consecutive Cases*, J Bone Joint Surg [Br]; 76–B:636–40 (Jul. 1994).

(List continued on next page.)

*Primary Examiner*—Paul J. Hirsch
*Assistant Examiner*—Michael B. Priddy
*Attorney, Agent, or Firm*—Baker Botts, L.L.P.

[57] ABSTRACT

The present invention is directed to novel two piece total elbow arthroplasty systems. In particular, the present invention is directed to total elbow implants, bone cutting guides for the installation of the implants, and methods for total elbow replacement. The apparatus and methods of the present invention are useful in the treatment of elbow osteoarthritis in canines, as well as in other species, including other quadrupeds and humans. The two piece implant of the present invention has an isometric humeral component and a radioulnar component that has an isometric articular surface. The components have stems for mounting in the medullary canals of the respective bones, which are angled so as to approximate the configuration of the original humerus, radius and ulna. In addition, novel cutting guides are provided to facilitate the removal of arthritic cartilage and a minimal amount of adjacent bone, thereby allowing the implantation of the two components (humeral and radioulnar), which are held in place by cement, such as polymethylmethylacrylate (PMMA). The result is a pain-free joint that has a near normal range of motion. Finally, the invention is directed to methods for implanting the novel endoprosthesis of the present invention in a canine elbow joint.

14 Claims, 15 Drawing Sheets

OTHER PUBLICATIONS

B.F. Morrey, et al., *Semiconstrained Elbow Replacement for Distal Humeral Nonunion*, J Bone Joint Surg [BR]; 77–B:67–72 (Jan. 1995).

J.A. Johnson, et al., *Incidence of Canine Appendicular Musculoskeletal Disorders in 16 Veterinary Teaching Hospitals from 1980 through 1989*, V.C.O.T. 7: 56–69 (1994).

B.A. Huibregtse, et al., *The Effect of Treatment of Fragmented Coronoid Process on the Developement of Osteoarthritis of the Elbow*, JAAHA 30:190–195 (Mar./Apr. 1994).

G.R. Bouck, et al.,*A Comparison of Surgical and Medical Treatment of Fragmented Coronoid Process and Osteochondritis Dissecans of the Canine Elbow*, V.C.O.T. 8: 177–83 (1995).

B.F. Morrey, et al., *Semiconstrained Arthroplasty for the Treatment of Rheumatoid Arthritis of the Elbow*, Journal of Bone and Joint Surgery, 74A:479–490 (Apr. 1992).

Olmstead, "The canine cemented modular total hip prosthesis, " *Journal of the American Animal Hospital Association*, vol. 31, Mar./Apr. 1995, pp. 109–124.

Sumner, et al., "Initial In Vitro Stability of the Tibial Component in a Canine Model of Cementless Total Knee Replacement," *Journal of Biomechanics*, vol. 27 No. 7, Jul. 1994, pp. 929–939.

Conzemius, et al., "Development and Evaluation of Semiconstrained Arthroplasty for the Treatment of Elbow Osteoarthritis in the Dog" Abstract in Veterinary and Comparative Orthopaedics and Traumatology, Apr. 1998, 11(4):A54.

Conzemius, et al., "Development and Evaluation of Semiconstrained Arthroplasty for the Treatment of Elbow Osteoarthritis in the Dog" Veterinary Orthopedic Society, 25th Annual Conference, Feb. 1998, p. 6.

Lewis, RH, "Development of Elbow Arthroplasty (Canine) Clinical Trials," *Proceedings from the 6th Annual ACVS Symposium*, San Francisco, CA, Oct. 1996, p. 110.

Lewis G, "The Elbow joint and its total arthroplasty. Part I. A state–of–art review," *Bio–Med Mater Eng*, 1996, 6:353–365.

Zafiropoulus et al., "An intramedullary aligned bone cutting jig for elbow replacement," *Med Eng Phys*, 1995, 17(2):111–114.

Photograph of multicomponent elbow endoprosthesis designed by Dr. Phil Vasseur et al. at the University of California at Davis, and believed to be in use on or before Dec. 1997.

TOTAL ELBOW ARTHROPLASTY SYSTEM

This application claims priority of provisional application No. 60/071,885, filed Dec. 31, 1997.

BACKGROUND OF THE INVENTION

1. Field of the Invention

The present invention relates to novel total elbow arthroplasty systems. In particular, the present invention is directed to total elbow implants, bone cutting guides for the installation of the implants, and methods for total elbow replacement. The apparatus and methods of the present invention are useful in the treatment of elbow osteoarthritis in canines, as well as in other species, including other quadrupeds and humans.

2. Description of the Background

Elbow osteoarthritis is the most common orthopedic problem of the front leg encountered by the small animal practitioner and veterinary surgeon. (Johnson J. A., et al., V.C.O.T. 7:56–69, 1994.) The etiology of elbow osteoarthritis (OA) is multifactorial, involving developmental conditions such as fragmentation of the medial coronoid process, osteochondrosis, asynchronous growth between the radius and ulna, ununited anconeal process, trauma and idiopathic causes. (Johnson J. A., et al., V.C.O.T. 7:56–69, 1994; Huibregtse B. A., et al., JAAHA 30:190–5, 1994.) The disease is frequently complicated by an early age of onset and patients that are bilaterally affected. (Huibregtse B. A., et al., JAAHA 30:190–5, 1994.) Medical (nonsteroidal anti-inflammatories and polysulfated glycosaminoglycans) and/ or surgical management of these conditions frequently leads to unsatisfactory results. Huibregtse et al. provide evidence that less than 50% of dogs treated medically and less than 60% of those treated surgically for fragmentation of the medial coronoid process had long-term successful recoveries. (Huibregtse B. A., et al., JAAHA 30:190–5, 1994.) Bouck et al. provided more objective data using force plate gait analysis and documented that lameness did not significantly improve from pretreatment status following medical or surgical therapy. (Bouck G. R., et al., V.C.O.T. 8:177–83, 1995.) Currently, no reliable alternative exists as a means to treat cases that have had unsatisfactory outcomes following medical or surgical management. In fact, none of the current methods of therapy are reliable as a primary therapy for elbow OA.

Improvements in implant designs and surgical techniques have made total elbow arthroplasty a satisfactory treatment for arthritic disorders of the elbow in man. (Kraay M. J., et al., J Bone Joint Surg [Br] 76-b:636–40, 1994.) In two separate evaluations, 91% of total elbow arthroplasty cases had long-term excellent outcomes. (Morrey, B. F., et al., J Bone Joint Surg [Br] 77-B:67–72, 1995.) (Morrey B. F., et al., J Bone Joint Surg [Am] 74-A:479–90, 1992.) Total elbow arthroplasty has been successfully used in man in cases of inflammatory arthritis, osteoarthritis, humeral non-union and erosive arthritis. (Kraay M. J., et al., J Bone Joint Surg [Br] 76-b:636–40, 1994.) (Morrey, B. F., et al., J Bone Joint Surg [Br] 77-B:67–72, 1995.) (Morrey B. F., et al., J Bone Joint Surg [Am] 74-A:479–90, 1992.)

Although a reliable canine total elbow replacement has not previously been available, total joint arthroplasty has been used in the hind limb of dogs. Specifically, total hip arthroplasty for OA is used in dogs with much success; 95% of dogs have a satisfactory outcome following total hip replacement. Canine total hip arthroplasty has been a multimillion dollar business in the U.S., Europe, and Japan for the last decade. Veterinarians and pet owners accept total joint replacement technology and the cost necessary to make it effective in the dog. The need for canine total elbow arthroplasty parallels that of canine total hip arthroplasty. In addition, many advances in human total knee arthroplasty are linked to successful research using canine models. (Sumner D. R., et al., J Biomechanics 27:929–39, 1994.)

In designing an elbow replacement, there are a number of special considerations. These include the fact that the elbow, unlike the hip or knee, is a three bone system requiring a three implant system or alteration of the existing bony structure. Left and right elbows are mirror images of each other; they are not isometric.

Technology and designs available for human total elbow arthroplasty, although helpful, cannot be directly applied to dogs because of significant anatomical and economical differences. Dogs are quadrupeds and their forelimbs are weight bearing; current total elbow implants used in humans are not designed to withstand the cyclic loading that would occur if used in a dog. In addition, canine bones have more contour than human bones and have increased variability in size and shape making cutting guides based upon the long axis of a bone difficult to use.

Total elbow arthroplasty in the dog is not commercially available, and has not been successfully attempted in the dog. A research group at the University of California at Davis led by Dr. Philip B. Vasseur devised a canine total elbow replacement system in 1995. The elbow replacement system was not studied in vivo before use in three client-owned dogs with naturally occurring elbow arthritis.

The system designed by Vasseur's group used three components, a humeral, a radial, and an ulnar component. The ulnar and humeral components articulated in a semi-constrained fashion. In effect, this means that the ulnar component loosely fit into the humeral component. The radial component articulated with both the humeral and ulnar components in an unconstrained manner. All three implants were designed and used for cemented fixation. All three components were non-isometric, or designed specifically for use in either the left or right limb.

Each of the three cases had an unsatisfactory result following total joint replacement because of implant failure. The research project was terminated (Personal communication with Dr. Vasseur on 10/96.) Malarticulation and loosening of the components led to decreased range of motion, inflammation and joint pain.

Another veterinary practitioner located in Lakeport, Calif., Ralph Lewis, has also designed and performed total elbow arthroplasty. The Lewis system is a constrained or hinged system which includes a humeral component, radioulnar component, a wrist pin screw and a locking screw. In order to install the implant, an osteotomy of the lateral epicondyle of the humerus and the proximal ulna are necessary. These osteotomies require repair with bone plates after the implants are installed.

In addition to requiring removal of a substantial amount of bone and subsequent bone repair, this system is also undesirable because the components are fully constrained (i.e., hinged). When constrained systems are loaded, the majority of the stress is shifted to the implant-cement or implant-bone interface. Constrained systems typically loosen at these stressed interfaces and thus have a much shorter lifespan than unconstrained or semiconstrained systems. Not only does this lead to implant failure, but it also makes FDA approval substantially more difficult to obtain.

Currently there is no total elbow arthroplasty system that satisfactorily manages difficult cases of canine elbow osteoarthritis. There is there fore a need for a canine total elbow replacement that provides a pain free joint which approximates normal range of motion.

SUMMARY OF THE INVENTION

The present invention overcomes the problems and disadvantages associated with current strategies and designs, and provides a total elbow replacement useful in the treatment of canine elbow arthritis with an improved long term prognosis.

The present invention incorporates the advantages of constrained and semiconstrained systems with isometry of the humeral component ( no left or right) and a 2-piece design (to implant on three bones). It is an unconstrained, modular, total elbow, designed for cemented application, and is suitable for uses including porous ingrowth.

Accordingly, one embodiment of the invention is directed to a two component elbow endoprosthesis comprising a humeral component and a radioulnar component. The humeral component has a condylar portion and a stem portion. The condylar portion is adapted to be received in a resected portion of a distal humerus between the medial and lateral aspects of the humeral condyle. The condylar portion ha s a proximal end and a distal end. A proximal portion is disposed at the proximal end; an isometric articulating surface, a medial side and a lateral side are disposed at the distal end. The proximal portion has a longitudinal axis and a first cross-sectional area. The articulating surface comprises arcuate groove disposed circumferentially along the distal end of the condylar portion, midway between the medial side and the lateral side. The humeral stem portion is attached to the proximal end of the proximal portion of the condylar portion. The stem portion is adapted to be received in the medullary canal of the distal humeral shaft. The humeral stem portion has a longitudinal axis which is angled cranially with respect to the longitudinal axis of the proximal portion of the condylar portion so that the condylar portion and stem portion approximate the original angle between the humeral condyle and the humeral shaft. In addition, the stem portion has a second cross sectional area which is smaller than the first cross-sectional area of the proximal portion, thereby forming a shoulder between the humeral stem portion and the proximal portion.

The radioulnar component is a single piece and is designed to articulate with the humeral component. The radioulnar component comprises a head portion comprising an isometric arcuate articulating ridge adapted to articulate with the arcuate groove of the humeral component, a radial stem portion attached to the head portion, which is adapted to be received in the medullary canal of a proximal radial shaft, and an ulnar stem portion attached to the head portion which is adapted to be received in the medullary canal of a proximal ulnar shaft.

The present invention is also directed to novel cutting guides used to install the implants of the present invention. These cutting guides are used to remove arthritic cartilage and adjacent bone, followed by implantation of two implants (humeral and radioulnar) which are held in place by polymethylmethylacrylate (PMMA). The result is a pain-free joint that has a near normal range of motion.

One embodiment of the invention is directed to a humeral cutting guide for removing the trochlea of the humerus, in order to prepare the humerus for implantation of an endoprosthetic joint. The cutting guide of this embodiment preferably comprises a proximal portion, a distal portion and a guide bar. The proximal portion has two parallel cutting slots through it. The distal portion has a first face. The proximal portion is affixed to the first face such that the proximal portion and distal portion are substantially perpendicular to each other. The guide bar is also disposed on the first face of the distal portion so that it is perpendicular to the first face and parallel to the proximal portion.

Another embodiment of the invention is directed to a radioulnar cutting guide for removing the articular surface of the radius and ulna, in order to prepare these bones for implantation of an endoprosthetic joint. This guide comprises an L-shaped member comprising a first limb and a second limb. The L-shaped member has a cutting surface comprising a first planar surface on the first limb, a second planar surface on the second limb perpendicular to the first planar surface, and a third curved surface disposed between the first and second surfaces. A proximal piece is affixed to the first limb. This proximal piece preferably has a first guide hole adapted for mounting on a pin in the proximal medullary canal of the ulna.

Finally, the present invention is directed to methods of using the implants and guides of the present invention. The system disclosed herein has clinical usefulness in veterinary medicine for the treatment of elbow arthritis. It is also useful for designing a live animal model for the study of implantology in human medicine, such as bioactive cement, porous ingrowth, hormone stimulation of bone ingrowth and aseptic loosening.

Another embodiment of the invention is directed to methods for implanting an elbow endoprosthesis in a canine elbow joint. One such method comprises the steps of removing the trochlea of the humerus, removing the articular surface of the ulna and radius and cancellous bone from the proximal medullary canals of the ulna and radius, and, in any order, inserting a radioulnar component into the medullary canals of the radius and ulna and affixing it in place, inserting bone graft between the proximal radius and ulna to encourage rapid synostosis, and inserting a humeral component into the medullary canal of the humerus and affixing it in place. In this method, the step of removing the trochlea may comprise the steps of drilling a first hole approximately 10 cm from the trochlear notch of the humerus proximally up the medullary canal, placing a first pin in the first hole until it engages cortical bone, mounting a cutting guide on the first pin, and removing the trochlea of the humerus. The step of removing the articular surface of the radius and ulna and cancellous bone may comprise the steps of placing an ulnar pin retrograde from an osteotomy at the mid-ulnar diaphysis through the ulnar shaft exiting at the olecranon, mounting a radioulnar cutting guide on the ulnar pin, removing the articular surface of the ulna and radius, and removing cancellous bone to a depth of about 1 cm from the medullary canal of the ulna and radius.

In a preferred embodiment of the method, the radioulnar component is installed first, and the step of inserting and affixing the humeral component comprises positioning a humeral component in the distal humeral shaft, reducing the radius and ulna, allowing articulation between the humeral and radioulnar components, flexing and extending the joint, allowing the humeral and radioulnar components to find a neutral position, and allowing the cement in the medullary canal of the humerus to harden.

Another embodiment is directed to a method for implanting an elbow endoprosthesis in a canine elbow joint, comprising the steps of drilling a first hole approximately 10 cm from the trochlear notch of the humerus proximally up the medullary canal, placing a first pin in the first hole until it engages cortical bone, mounting a cutting guide on the first pin, removing the trochlea of the humerus, removing the cutting guide, placing a second pin retrograde from the mid-ulnar diaphysis through the ulnar shaft exiting at the olecranon, mounting a radioulnar cutting guide on the second pin, removing the articular surface of the ulna and radius, removing cancellous bone to a depth of about 1 cm from the medullary canal of the ulna and radius, placing a cement, such as PMMA, into the medullary canals of the radius and ulna, inserting a radioulnar component and holding it in place until the cement hardens, inserting bone graft between the proximal radius and ulna to encourage rapid synostosis, placing cement into the medullary canal of the humeral shaft, positioning a humeral component in the distal humeral shaft, reducing the radius and ulna, allowing articulation between the humeral and radioulnar components, flexing and extending the joint, allowing the humeral and radioulnar components to find a neutral position, and allowing the cement in the medullary canal of the humerus to harden.

Other embodiments and advantages of the invention are set forth, in part, in the description which follows, and, in part, will be obvious from this description and may be learned from the practice of the invention.

DESCRIPTION OF THE INVENTION

As embodied and broadly described herein, the present invention is directed to novel apparatus and methods for total elbow arthroplasty in the dog. The present invention relates to total elbow implants, bone cutting guides for the installation of the implants, and methods for total elbow replacement. The apparatus and methods of the present invention are useful in the treatment of elbow osteoarthritis in canines, as well as in other species, including other quadrupeds and humans.

As will be understood by those skilled in the art, the following terms as used herein have the following meanings:

median plane—a plane which longitudinally divides the animal into equal right and left halves; the term may also be used to refer to dividing a limb along its axis.

cranial—toward or relatively closer to the head.

caudal—toward or relatively closer to the tail.

dorsal—toward or relatively closer to the back (top) of the head, neck, trunk, or tail.

ventral—toward or relatively closer to the underside of the head, neck, trunk, or tail.

medial—toward or relatively closer to the median plane.

lateral—away from or relatively further from the median plane.

proximal—when used in reference to the limbs it implies a position near or relatively closer to the trunk.

distal—when used in reference to the limbs it implies a position away from or relatively further from the trunk.

Implants

Figure 1:
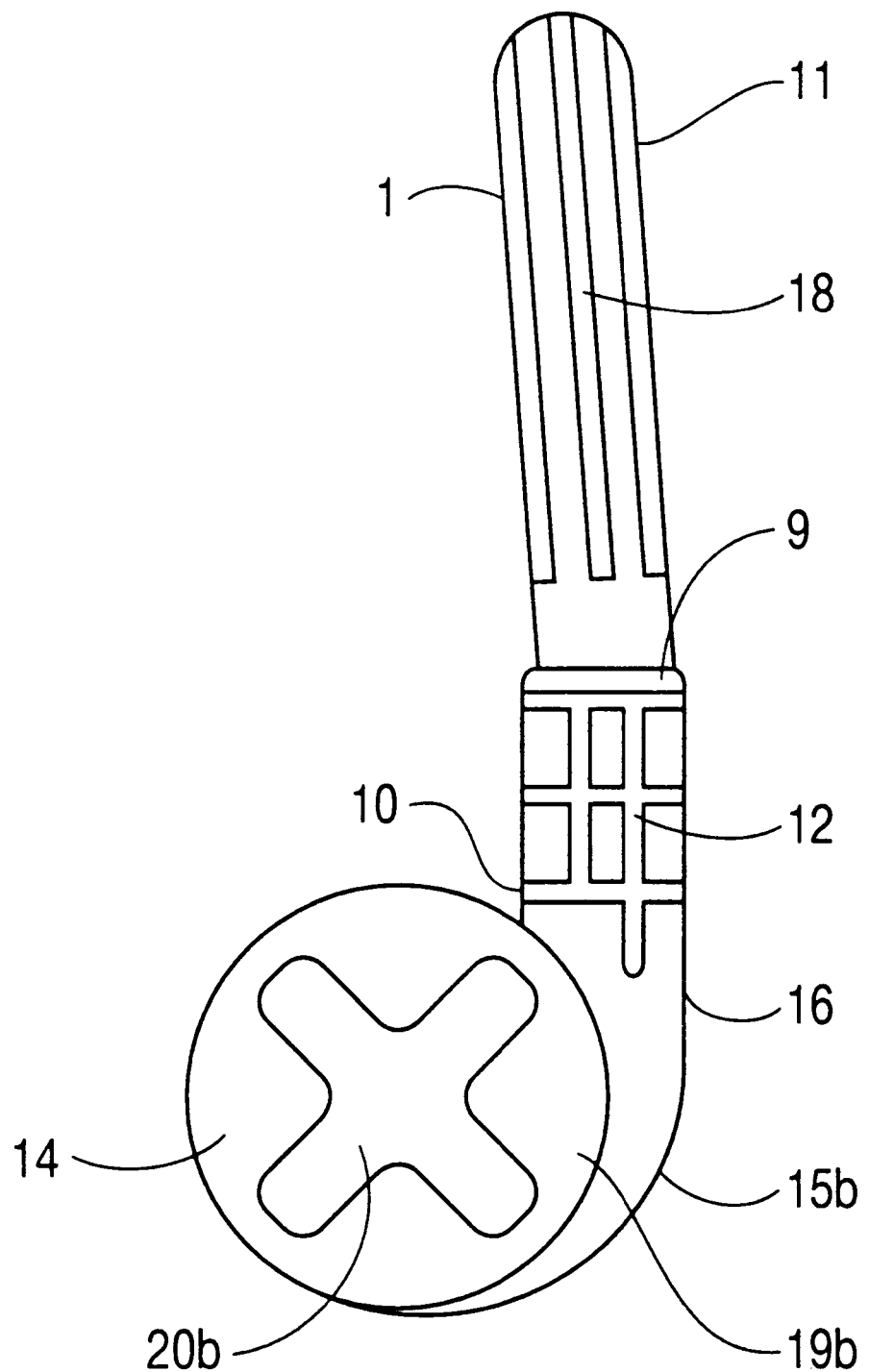
FIG. 1 is a lateral view of the humeral component of the present invention.
Figure 2:
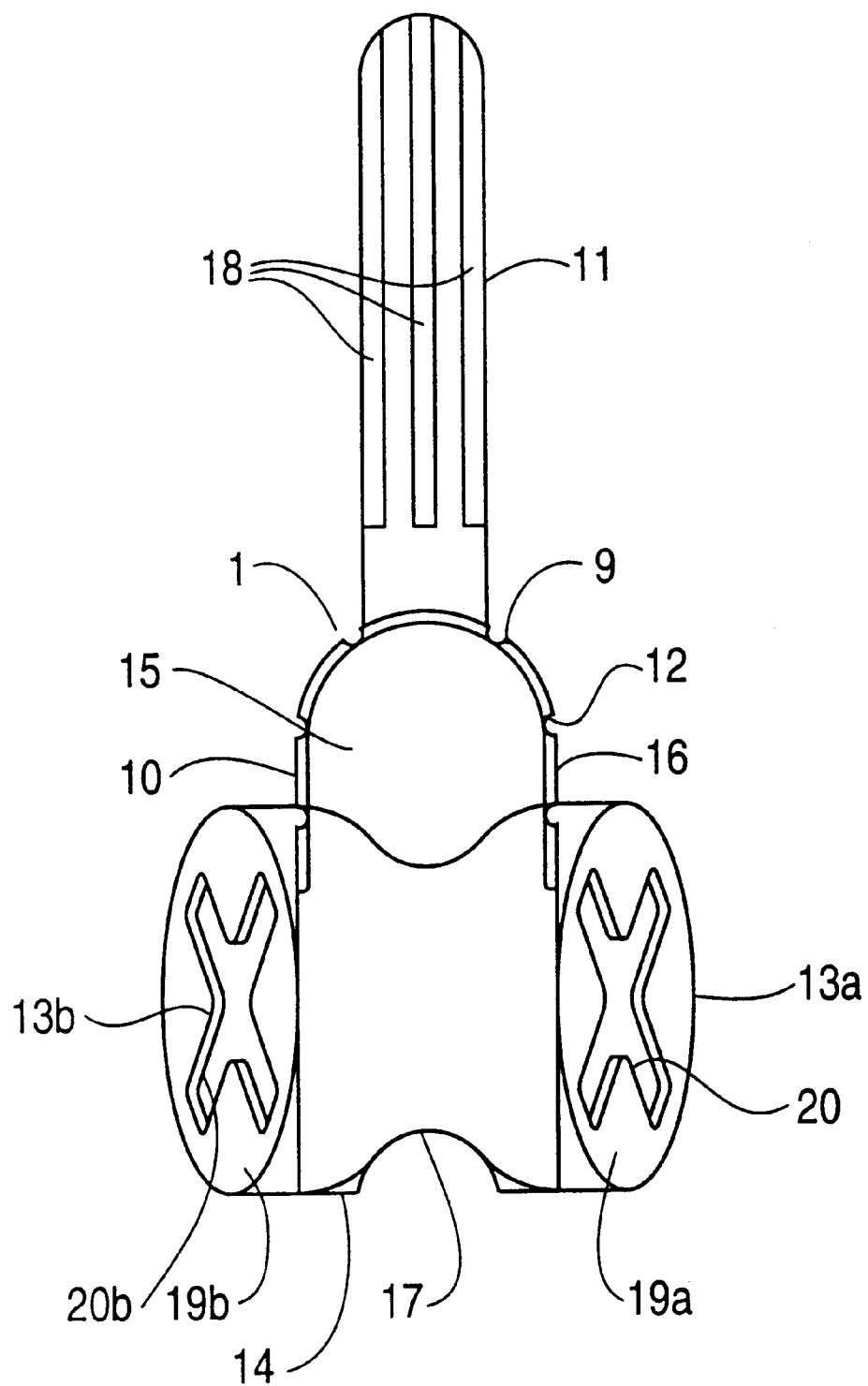
FIG. 2 is a caudal view of the humeral component of the present invention.
Figure 3:
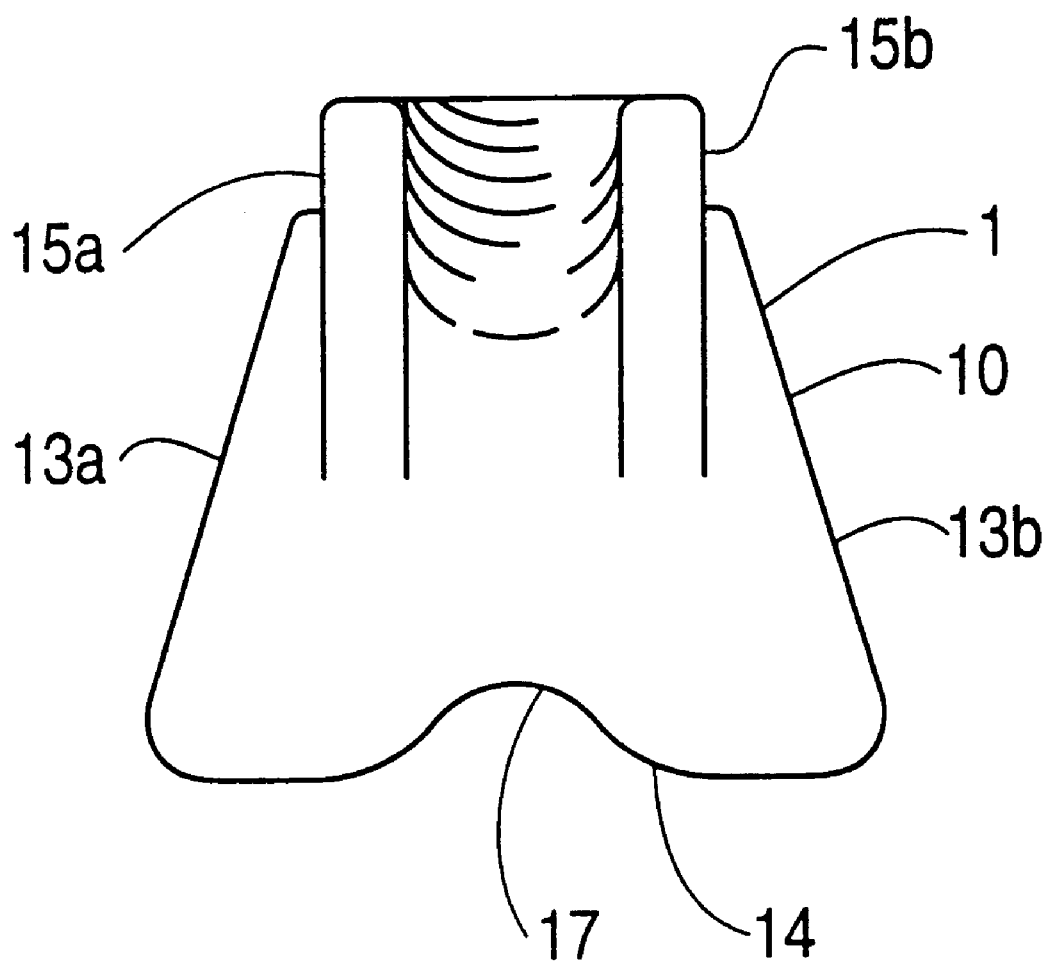
FIG. 3 is a ventral view of the humeral component of the present invention.

The total elbow implants of the present invention include a humeral component 1 and a radioulnar component 2. FIGS. 1–3 depict the humeral component of the elbow implant of the present invention. FIG. 1 is a lateral view of humeral component 1. FIG. 2 is a caudal view of humeral component 1. FIG. 3 is a ventral view of humeral component 1.

Referring to FIGS. 1–3, humeral component 1 comprises a humeral stem portion 11 and a humeral condylar portion 10. Stem portion 11 is positioned with respect to condylar portion 10 such that it lies at an angle that matches the relationship between the original humeral condyle and the humeral shaft. In a preferred embodiment, the longitudinal axis of stem portion 11 is angled cranially 5 degrees with respect to the longitudinal axis of proximal portion 16 of condylar portion 10. Thus, as can be seen in FIG. 1, the proximal end of stem portion 11 is more cranial than its distal attachment to proximal portion 16. In a preferred embodiment, stem portion 11 is rounded at its most proximal end, and has grooves 18 running along its longitudinal axis to facilitate cementing of the component into position.

Humeral condylar portion 10 comprises a proximal portion 16 at its proximal end, and an articulating surface 14, two humeral ridges 15a and 15b and two sides (flanges) 13a (medial side) and 13b (lateral side) at its distal end. Stem portion 11 is attached to proximal portion 16. Proximal portion 16 preferably has a greater cross-sectional area than stem portion 11, thereby forming a shoulder 9 at the junction between them.

As can be best appreciated in FIGS. 2–3, sides 13a and 13b have planar surfaces 19a and 19b, which are each angled approximately 14 degrees towards the median plane of the implant, so that they are farther apart cranially than they are caudally, thereby matching the cut surfaces of the bone. As best shown in FIGS. 1–2, X-shaped grooves 20a and 20b are disposed in planar surfaces 19a and 19b and may have a reverse wedge or dovetail design to facilitate the interlocking of cement into the implant. Planar surfaces 19a and 19b of sides 13a and 13b are preferably round around their outer peripheries. These are articulating surfaces so sharp edges are preferably avoided.

To facilitate fixation, grooves 12 may be provided on proximal portion 16 of humeral condylar portion 10. In a preferred embodiment, grooves 12 run both longitudinally and transversely on proximal portion 16. The grooves preferably have a reverse wedge design, with an outside diameter smaller than the inside diameter, thereby allowing for cement to be locked in place. For example, the outside diameter of the grooves may be 2 mm or greater, which allows for the cement mantle to be 2 mm or greater. A cement mantle of at least 2 mm provides mechanical strength of the cement. Grooves 18, on stem portion 11, like grooves 12, may also have a reverse wedge design.

Articulating surface 14 is disposed on the distal aspect of condylar portion 10 between sides 13a and 13b. Articulating surface 14 comprises a arcuate groove 17 (disposed circumferentially along a median plane through the distal end of condylar portion 10, midway between sides 13a and 13b). Viewed end on, arcuate groove 17 has a flared C-shaped profile. As with the other articulating surfaces, sharp edges are preferably avoided.

Articulating surface 14 has no corners, thereby reducing wear. The curvature and profile of arcuate groove 17 matches the curvature and profile of articulating ridge 24 of radioulnar component 2, discussed below, thereby allowing for smooth articulation. The radius of curvature of the two components is smooth enough that medial and lateral rotation and cranial and caudal translation are possible. Because such motions are allowed, the system is nonconstrained.

Nonconstrained systems have no mechanical linkage between the implants and rely on the natural ligaments of the body for stability. An advantage of the design of the present invention is reduced wear between the components and reduced stress at the component-cement and cement-bone interfaces. This increases lifespan of the implants. The articulating surfaces of the components allow smooth articulation and greater range of motion in flexion and extension than in even the normal joint. This eliminates the likelihood of binding during use.

Humeral ridges 15a and 15b are disposed along the caudal aspect of humeral component 1. These ridges extend cranially approximately half-way along the ventral surface of humeral component 1, and lie on either side of the caudal aspect of groove 17. Humeral ridges 15a and 15b do not articulate with radioulnar component 2 unless the joint is in full extension. Elbow joints, which rarely luxate, luxate when in full extension. The additional articulation provided by ridges 15a and 15b provides resistance in a mediolateral direction between the implants, thereby decreasing the likelihood of traumatic luxation. Because ridges 15a and 15b do not articulate during normal weight bearing range of motion, they do not constrain the implants during use.

As can be seen from FIGS. 1–3, the humeral component of the preferred embodiment is entirely isometric, and can be used in either joint.

Figure 4:
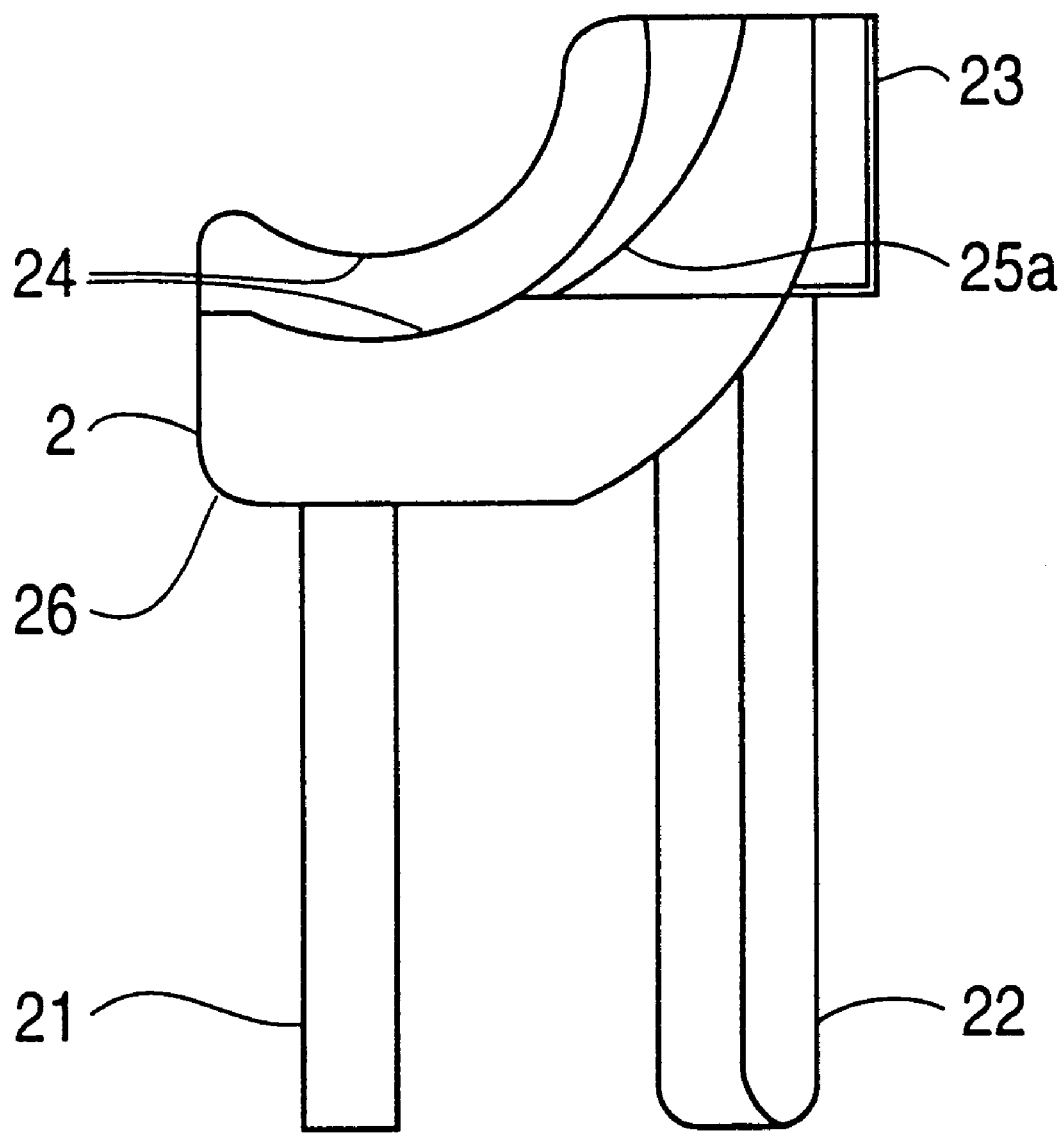
FIG. 4 is a lateral view of the radioulnar component of the present invention.
Figure 5:
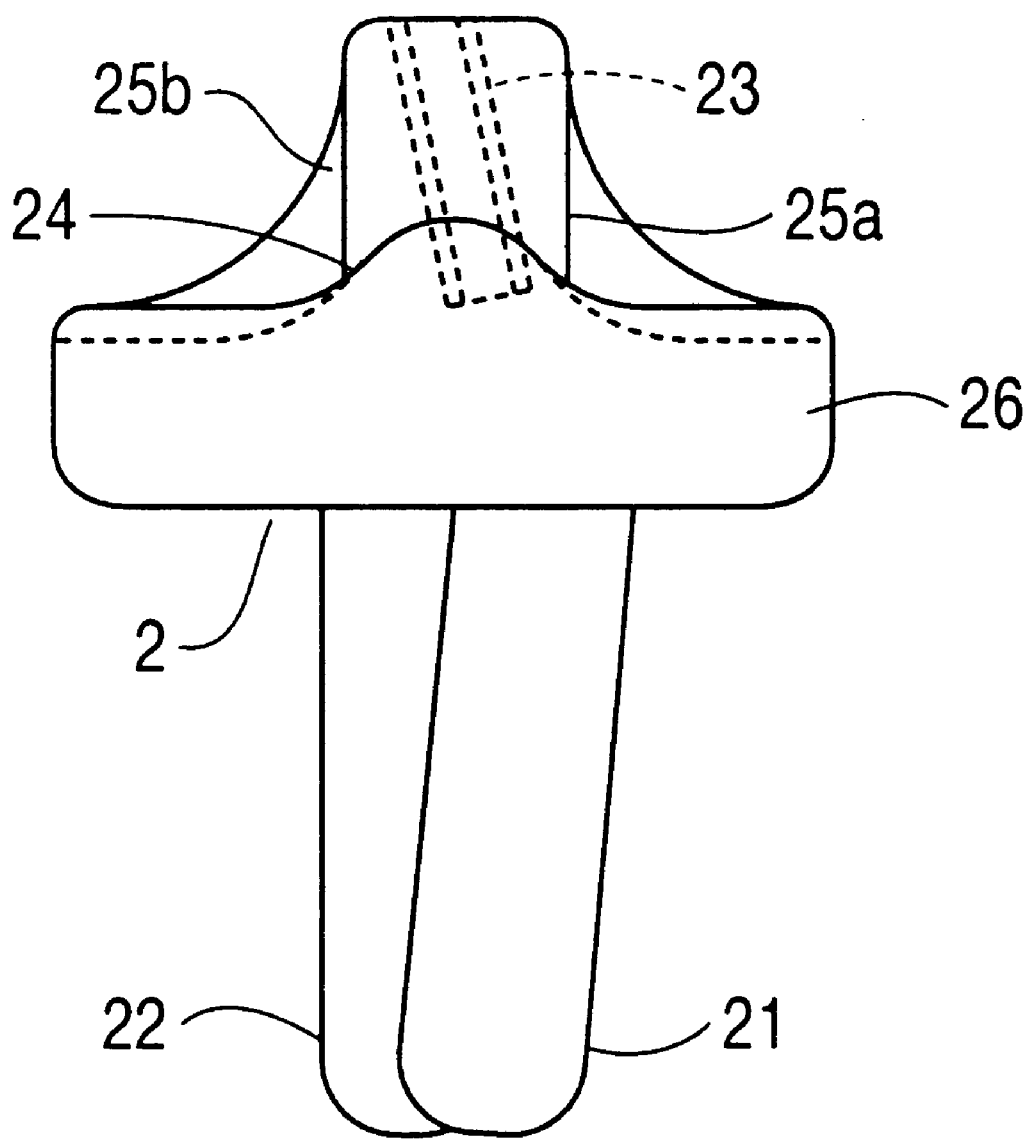
FIG. 5 is a cranial view of the radioulnar component of the present invention.
Figure 6:
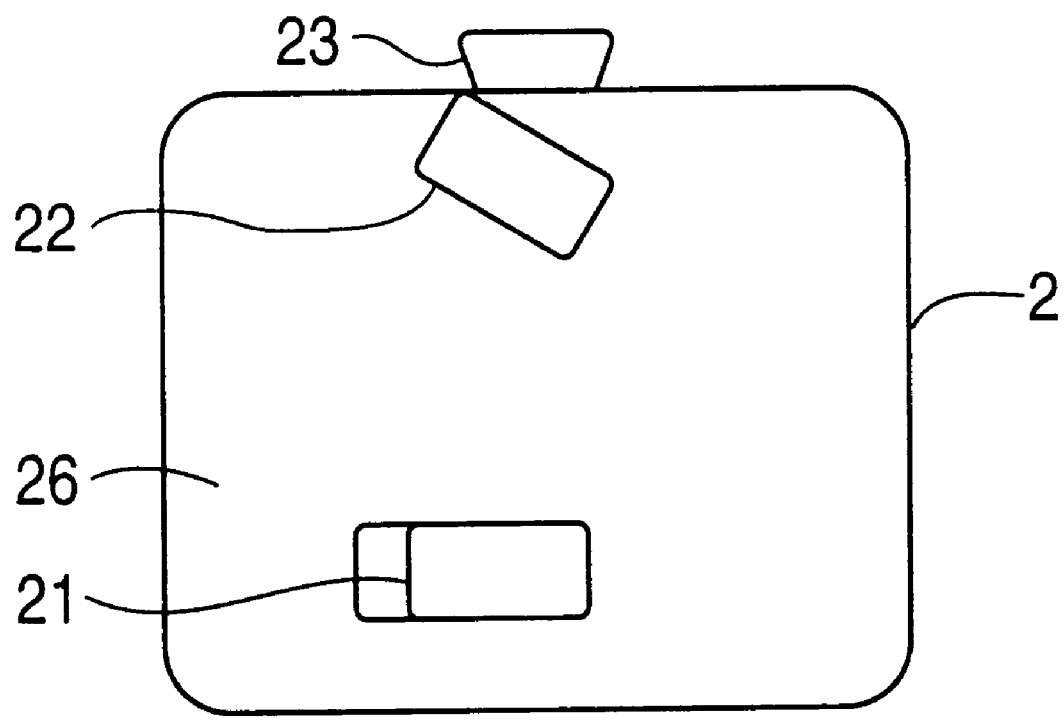
FIG. 6 is a ventral view of the radioulnar component of the present invention.

FIGS. 4–6 depict the radioulnar component of a preferred embodiment of the present invention. The radioulnar component is a single piece designed to articulate with the humeral component. FIG. 4 is a lateral view of radioulnar component 2 for use on a left elbow. FIG. 5 is a cranial view of radioulnar component 2. FIG. 6 is a ventral view of radioulnar component 2.

Referring to FIGS. 4–6, radioulnar component 2 comprises a radial stem 21, an ulnar stem 22, and a head portion 26 comprising an ulnar hook 23, articulating ridge 24 and radioulnar grooves 25a and 25b.

Radial stem 21 comes off head portion 26 of radioulnar component 2 at an angle that matches the relationship between the original radial head and radial shaft. As most clearly depicted in FIG. 5, radial stem 21 has a rectangular cross section with rounded edges, and is preferably angled 5 degrees medially (or to the left of the longitudinal axis of a left radiuolnar component when the component is viewed from its cranial aspect). Thus, as can be seen in FIG. 5, the distal end of radial stem 21 is more medial than its proximal attachment to head portion 26. Ulnar stem 22 comes off head portion 26 of radioulnar component 2 at an angle that matches the relationship between the original ulna and ulnar shaft. As best seen in FIG. 6, ulnar stem 22 has a rectangular cross section with rounded edges. Ulnar stem 22 has a longitudinal axis which is generally coaxial with the longitudinal axis of the implant, but the lateral aspect of stem 22 is preferably angled 30 degrees towards the medial side of the implant. For example, when a left radioulnar component is viewed ventrally, the stem is rotated clockwise around its longitudinal axis, so that the lateral aspect of the stem is rotated caudally towards the medial side of the implant and the medial aspect of the stem is rotated cranially towards the lateral side of the implant. As can be seen from FIGS. 4–6, radial stem 21 and ulnar stem 22 are configured with respect to each other and to head portion 26 to match or be compatible with the normal anatomical relationship of the medullary canals and articular surfaces of these two bones. In a preferred embodiment, either or both stems 21 and 22 are rounded at their distal extremities. The stems are cemented in place to help stabilize the component.

Ulnar hook 23 comes off the caudal aspect of head portion 26 of radioulnar component 2 at an angle that follows the natural curvature of the proximal ulna. Specifically, the proximal portion of ulnar hook 23 is rotated approximately 13.05 degrees medially with respect to vertical. Hook 23 has a reverse wedge shape and is cemented in place. This further helps stabilize radioulnar component 2.

Articulating ridge 24 is disposed on the cranial proximal aspect of head portion 26 of radioulnar component 2. Articulating ridge 24 is isometric and has a flared C-shape which matches the profile of articulating surface 14 of humeral component 1. Articulating ridge 24 has no corners which will reduce wear and constraint when articulating with articulating surface 14 of humeral component 1.

Radioulnar grooves 25a and 25b are disposed on radial head portion 26 on each side of (medial and lateral to) articulating ridge 24. These grooves do not articulate with humeral component 1 unless the joint is in full extension. The additional articulation of grooves 25a and 25b provides resistance in a mediolateral direction between components 1 and 2 which decreases the likelihood of traumatic luxation. As grooves 25a and 25b do not articulate during normal weight bearing range of motion, they do not constrain the implants during use.

Although FIGS. 4–6 depict a radioulnar component for use in a left canine elbow, as will be clear to those of skill in the art, a mirror image of radioulnar component 2 depicted in FIGS. 4–6 can be used in the opposite elbow.

In a preferred embodiment, humeral component 1 is isometric and machined from Grade 5 titanium or molded from a cobalt-chromium alloy. The humeral component may be altered for composite stabilization by surface treatment of the component where it is in direct contact with bone. Radioulnar component 2 may be made of any suitable material, but is preferably made of medical grade non-crosslinked ultra-high molecular weight polyethylene ("UHMWPE"). Other suitable materials for the components may be used, including titanium, cobalt-chromium or ceramic. Both implants may be either hand machined and polished, or molded.

In the preferred embodiment, the implant system allows motion in more than one plane between the two implants. The articulation between the implant allows approximately 150 degrees of flexion-extension, 1 mm of mediolateral translation, 2 mm of craniocaudal translation, and 8 degrees of pronation and supination. Constrained systems (e.g., hinge) have unsuccessful long term outcomes in cycled, loaded systems.

Cutting Guides

As discussed in more detail in the Examples which follow, implantation of the joint of the present invention is facilitated using the novel cutting guides of the present invention. Preferred embodiments of these guides are depicted in FIGS. 7–15.

Figure 7:
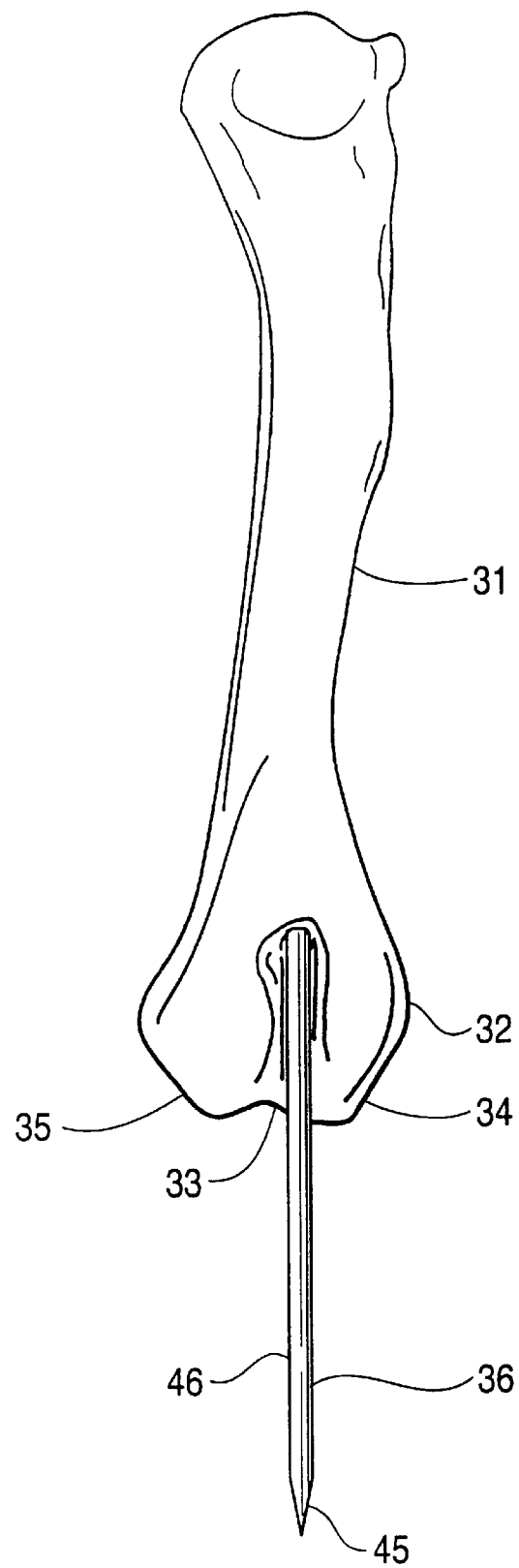
FIG. 7 is a caudal view of a left canine humerus with an intramedullary nail.

FIGS. 7–12 depict the humeral cutting guide of the present invention and its use. FIG. 7 is a caudal view of a left canine humerus 31 with intramedullary nail 36 inserted. As depicted in FIG. 7, humerus 31 has a condyle 32 at its distal end. The trochlea 33 of humerus 31 is the articular surface of the humerus. This is a potential location of arthritic cartilage in an arthritic elbow joint, and needs to be removed in connection with installing humeral component 1 of the present invention. The medial collateral ligament attaches to the medial aspect of the humerus at point of insertion 35, and the lateral collateral ligament attaches to the lateral aspect of the humerus at point of insertion 34.

Figure 8:
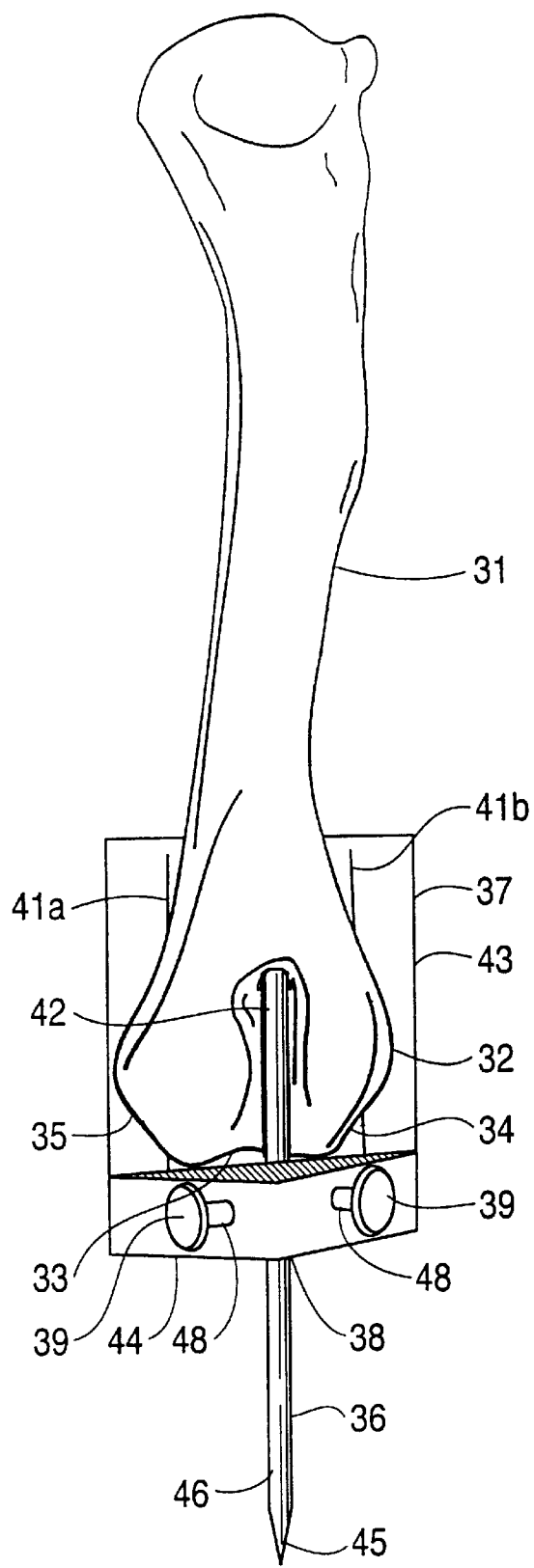
FIG. 8 is a caudal view of a canine humerus with the humeral cutting guide of the present invention for use on the left elbow mounted on the intramedullary nail.
Figure 9:
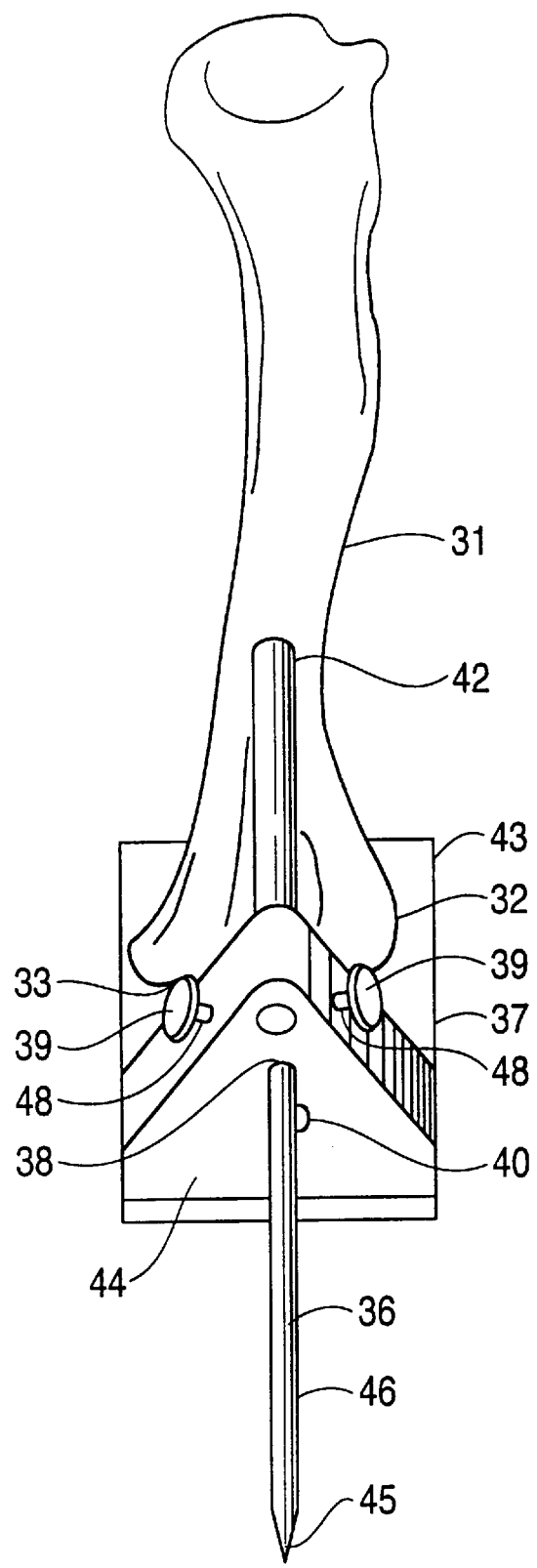
FIG. 9 is a dorsocaudal view of the humerus with the cutting guide mounted on the intramedullary nail.
Figure 10:
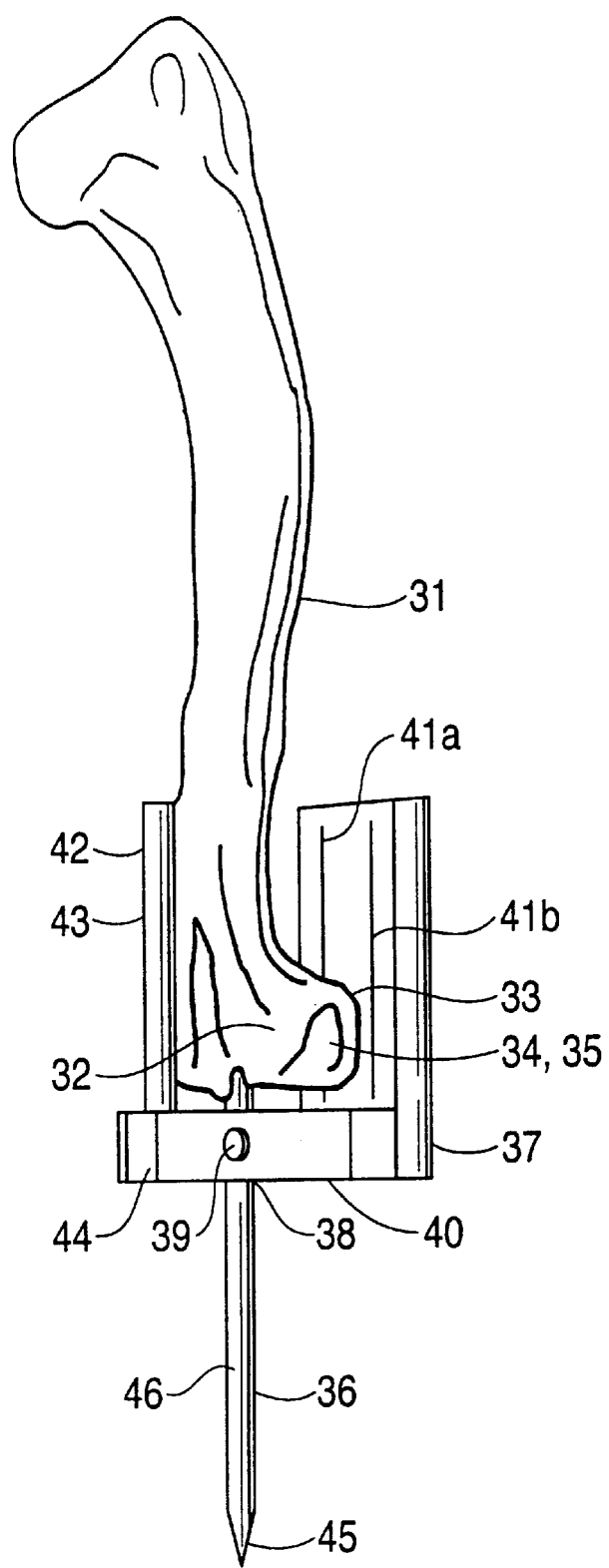
FIG. 10 is a side view of the humerus with the cutting guide mounted on the intramedullary nail.

FIG. 8 is a caudal view of humerus 31 with cutting guide 37 mounted on intramedullary nail 36. FIG. 9 is a dorso-caudal view of humerus 31 with cutting guide 37 mounted on intramedullary nail 36. FIG. 10 is a side view of humerus 31 with cutting guide 37 mounted on intramedullary nail 36.

As depicted in FIGS. 8–10, humeral cutting guide 37 has proximal or upper portion or plate 43 attached to a distal or lower articular portion or plate 44. Upper or proximal portion 43 and lower or distal portion 44 are preferably planar and disposed roughly perpendicular to each other. In a preferred embodiment, lower portion 44 is wedge shaped at the end opposite the end which is attached to upper portion 43. Humeral cutting guide 37 is designed to be mounted on intramedullary nail 36 which is placed from the middle of the humeral trochlea 33 into the medullary canal of the humerus. Intramedullary nail 36 allows for mounting of cutting guide 37 on the neutral axis of the humerus. Intramedullary nail 36 preferably has a trochar tip 45 which allows for easy passage into the medullary canal. Nail 36 also preferably has flattened sides 46 to facilitate immobilization and prevent undue rotation when screws 39 in cutting guide 37 are tightened.

Referring again to FIGS. 8–10, humeral cutting guide 37 has intramedullary nail pilot hole 38 through lower portion 44. Intramedullary nail 36 is placed through nail pilot hole 38 in order to mount cutting guide 37 onto the humerus 31. To further secure cutting guide 37, screws 39 are disposed on the lower portion 44 of cutting guide 37 through screw holes 48. Screws 39 are tightened into nail 36 to prevent rotation of cutting guide 37. Cutting guide 37 further has a pin pilot hole 40 in lower portion 44, through which pin 50 may be drilled to further prevent rotation of cutting guide 37.

Cutting guide slots 41a and 41b are disposed on upper portion 43 of cutting guide 37, and are located medial to the points of insertion 34 and 35 of the collateral ligaments of the humerus. Cutting guide slots 41a and 41b are parallel to each other and to cutting guide bar 42, which is disposed on the lower portion of cutting guide 37 to guide the saw used to prepare the humerus for the implants.

A saw, such as a reciprocating saw, is placed through cutting guide slots 41a and 41b to the level of cutting guide bar 42. The tip of the saw rests on bar 42 as cuts are made. This places the saw in the appropriate angle so that all articular cartilage on the trochlea of the humerus can be removed. The cutting slots 41a and 41b are located medial to the insertion points 34 and 35 of the collateral ligaments and the saw cuts are made away from the ligaments, which helps to ensure natural ligament stability of the joint after surgery. Specifically, cuts are made in the humerus using the two slots 41a and 41b of the guide. The amount of bone removed and the angles created in the condyle match the angles on sides 13a and 13b of humeral component 1.

Figure 11:
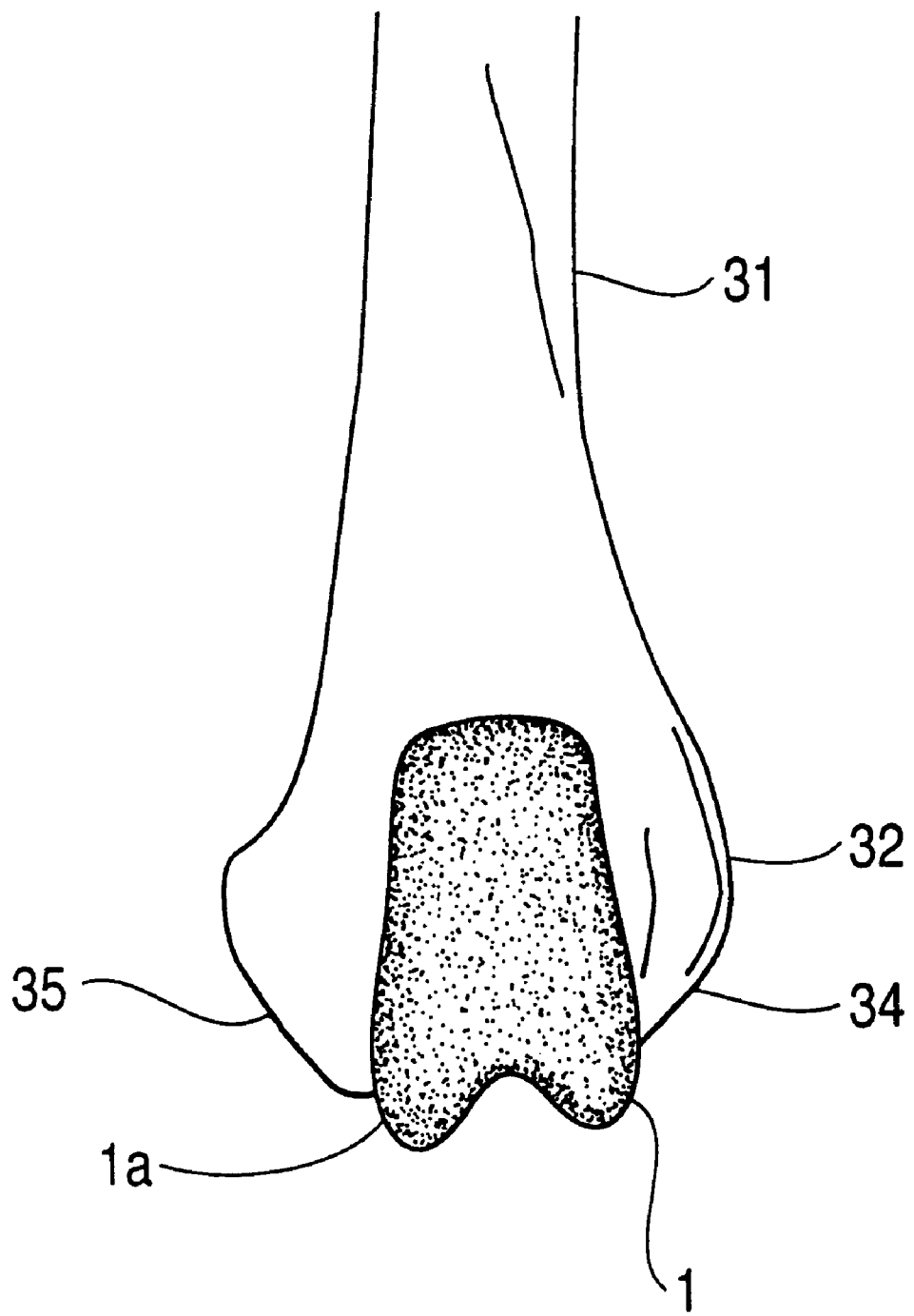
FIG. 11 is a caudal view of a canine humerus with the humeral component of the present invention in place.
Figure 12:
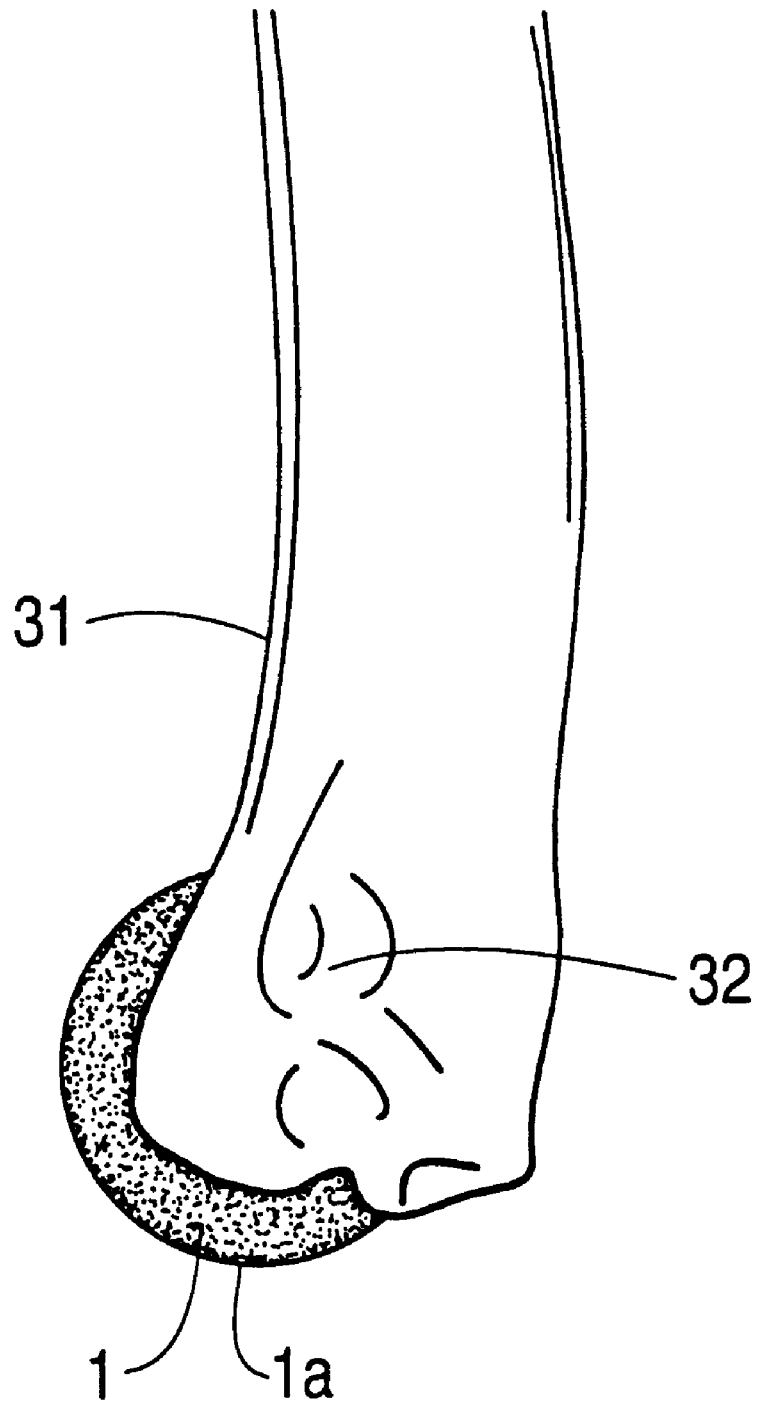
FIG. 12 is a side view of the humerus with the humeral component in place.

FIG. 11 is a caudal view of humerus 31 with humeral component 1 of the implant in place. FIG. 12 is a side view of humerus 31 with the humeral component 1 in place. As depicted in FIGS. 11–12, the sides of humeral component 1 when installed, will nearly approximate the cut edge of the humeral condyle. Any discrepancy may be filled in with bone cement. The humeral component edge 1a is just below the level of the remaining condyle, allowing for full range of motion without impingement on bone.

Figure 13:
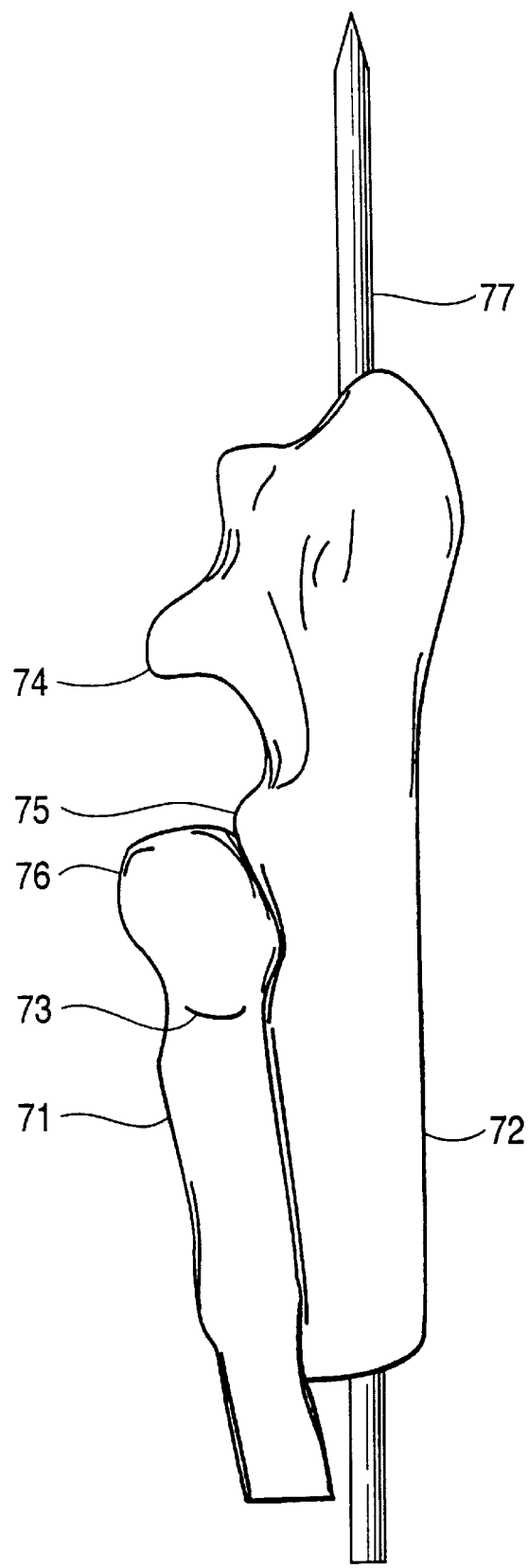
FIG. 13 is a side view of a left radius and ulna with an ulnar pin disposed in the ulnar medullary canal.
Figure 14:
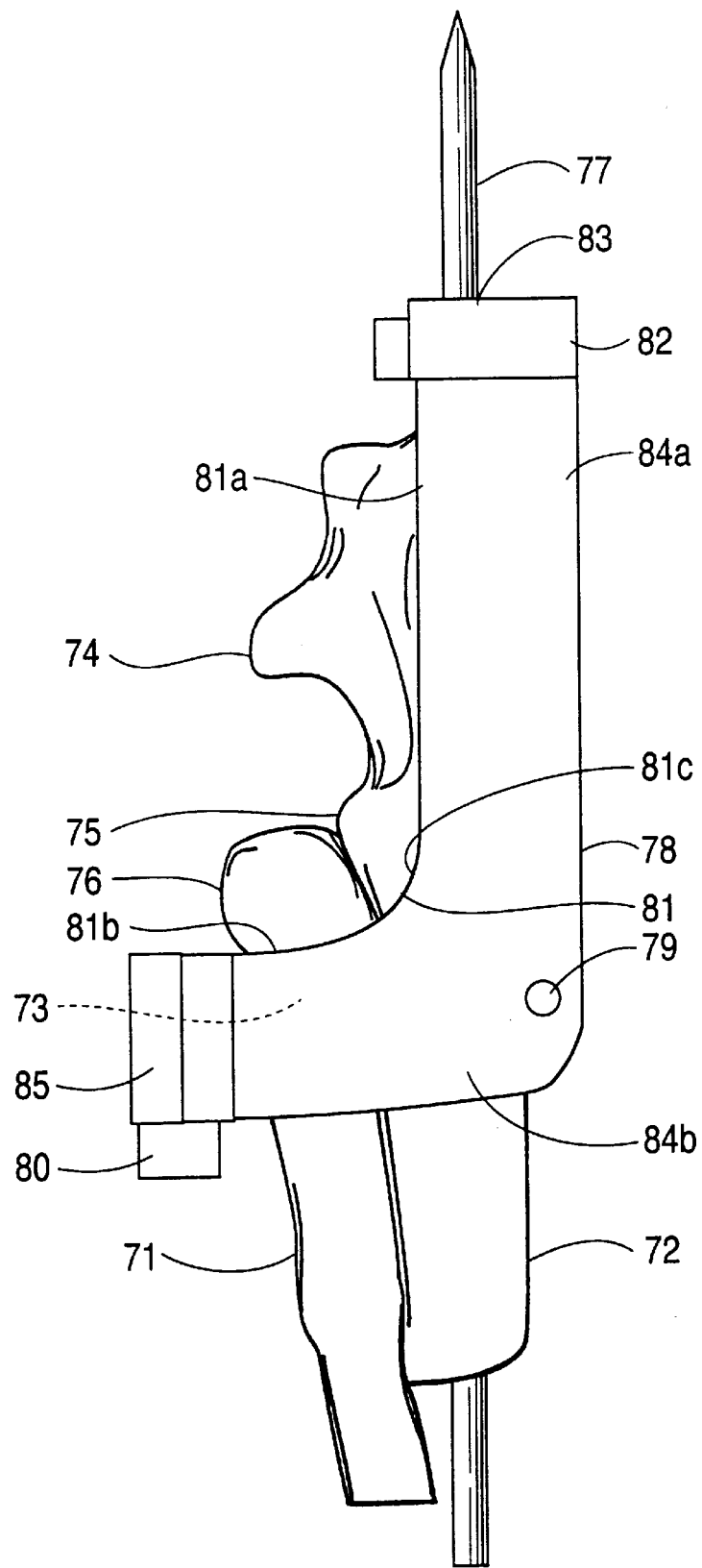
FIG. 14 is a side view of a radius and an ulna with the radioulnar cutting guide of the present invention for use on the left elbow mounted on the ulnar pin.
Figure 15:
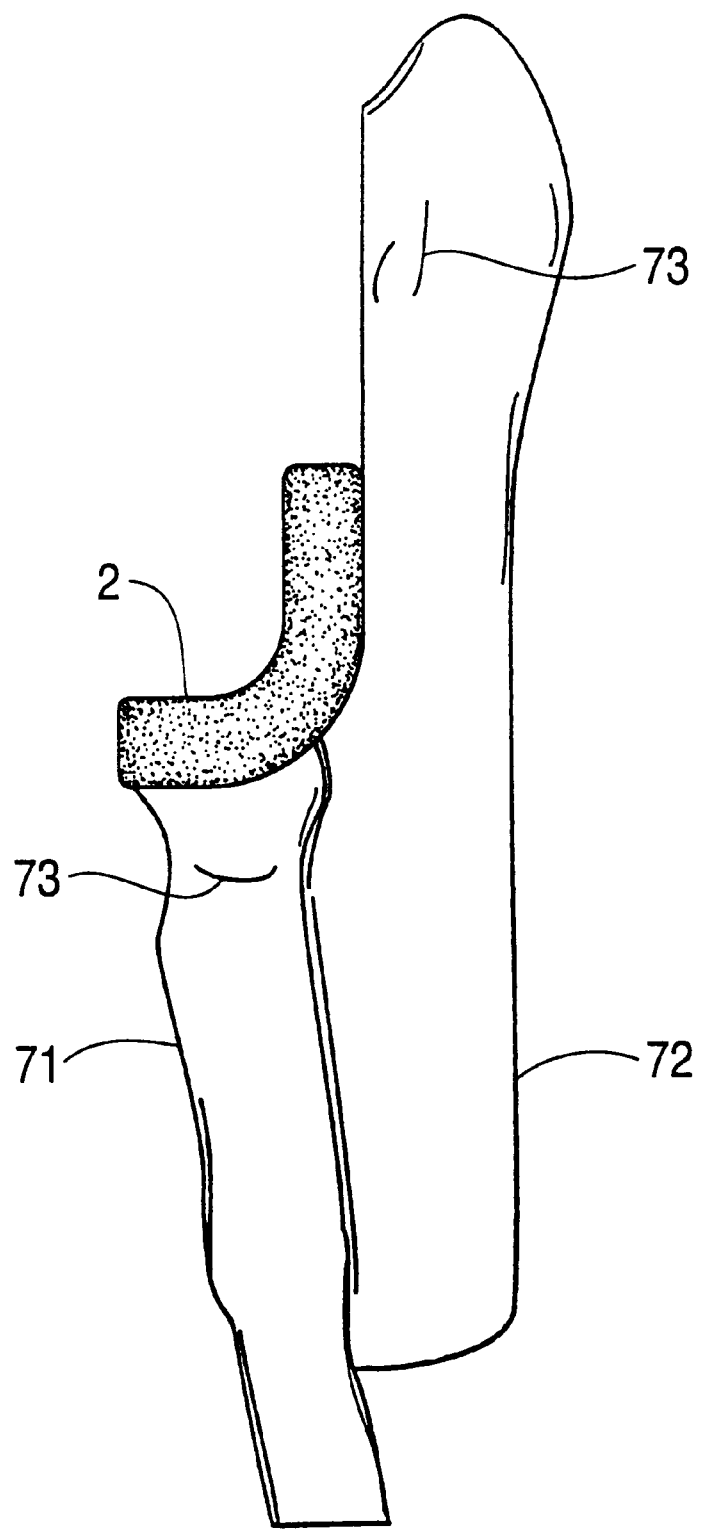
FIG. 15 is a side view of a radius and an ulna with the radioulnar component of the present invention in place.

FIGS. 13–15 depict the radioulnar cutting guide of the present invention and its use. FIG. 13 is a side view of left radius 71 and left ulna 72 with ulnar pin 77 disposed in the ulnar medullary canal. The radial collateral ligament attaches to the radius at point of insertion 73. The articular surfaces of the ulna include anconeal process 74 and coronoid process 75. The articular surface of the radius is radial head 76. These three articular sites are potential locations of arthritic cartilage in an arthritic elbow joint, and are removed in connection with installing the radioulnar component of the implant of the present invention.

An osteotomy is performed at the mid-ulnar diaphysis. Following the osteotomy, ulnar pin 77 is placed in retrograde fashion from the osteotomy cut site distally up the ulnar medullary canal and out the olecranon. Radioulnar cutting guide 78 is mounted on ulnar pin 77. The pin location reproducibly places cutting guide 78 so that the articular cartilage can be removed from the ulna. When cutting guide 78 rests on the olecranon, it reproducibly locates the cutting guide to a level in which the articular cartilage of the radial head will be removed, but the collateral ligaments are protected from damage.

FIG. 14 is a side view of radius 71, ulna 72 with radioulnar cutting guide 78 mounted on ulnar pin 77. As can be seen from FIG. 14, radioulnar cutting guide 78 is roughly L-shaped, with a first limb 84a perpendicular to second limb 84b. Top portion 82 is attached to the proximal end of first limb 84a and extends medially from its point of attachment to first limb 84a. Top portion 82 preferably has a guide hole 83 for receiving ulnar pin 77. Radioulnar cutting guide 78 has a cutting surface 81 comprising first flat cutting surface 81a, second flat cutting surface 81b and curved cutting surface 81c. First and second flat cutting surfaces 81a and 81b allow for the arthritic cartilage associated with the radial head, coronoid process, and anconeal process to be removed. In addition, cutting surface 81 has a unique curved cutting surface 81c disposed between first and second flat cutting surfaces 81a and 81b, thereby allowing for a curved cut at the distal point of the ulna. This feature preserves bone stock and decreases the stress concentration at this site as compared to a squared cut.

Lateral pilot hole 79 is disposed on the lateral aspect of radioulnar cutting guide 78, preferably at the intersection between first limb 84a and second limb 84b. Bottom portion 85 is disposed on the cranial end of second limb 84b and extends medially from its point of attachment to second limb 84b. Cranial pilot hole 80 is disposed on bottom portion 85.

A pin may be placed through lateral pilot hole 79 into the ulna once the cutting guide is appropriately placed to reduce rotation of the cutting guide. A second pin may be placed through cranial pilot hole 80 into the cranial aspect of the radius once the guide is appropriately placed to further reduce rotation of the cutting guide.

FIG. 15 is a side view of radius 71 and ulna 72 with radioulnar component 2 in place. As can be seen in FIG. 15, radioulnar component 2 rests on the cut surfaces of the radius and ulna. The articulation surface of the component is similar to the natural, original curvature of the intact radius and ulna. Radioulnar component 2 does not include a radius as great as the original ulna. This decreases the constraint of the system when radioulnar component 2 and humeral component 1 articulate allowing for increased forces to be absorbed by the ligaments of the joint, thereby increasing component lifespan.

FIGS. 1–15 depict the cutting guides and implants being used in a left canine elbow. As will be clear to those of skill in the art, the present invention can be modified for use in humans and other species. The cutting guide for the humerus depicted in FIGS. 7–10 is isometric and may be used to prepare the left or right elbow. As depicted in FIG. 14, the cutting guide for the radius and ulna in the preferred embodiment is not isometric. Instead, the cutting guide for the right elbow is essentially a mirror image of the one shown in FIG. 14. Alternately, in another embodiment, a singular radioulnar cutting guide may be used. In this embodiment, the guide has a removable top portion 82 that can be flipped over, putting guide hole 83 in alignment for use on either elbow. Likewise, a removable bottom portion 85 is provided that can be flipped over, putting guide hole 80 in alignment for use on either joint.

The bone cutting guides are used to prepare the bones of the elbow joint for implantation of the implants. This design allows the humeral implant to be isometric (i.e., can be used in either left or right elbow). The radioulnar implants are preferably mirror images, individually tailored to the right and left joints. Since many more implants (single use) than bone cutting guides (multiple use) will be made, the design features of the present invention provide improved and necessary cost efficiency.

The cutting guides depicted in FIGS. 7–15 may be made from any suitable material, such as stainless steel. In the preferred embodiment, they are made from 316 L stainless steel. The steel is preferably hand machined and polished to form the cutting guides and then heat treated for hardening.

Dogs with elbow OA generally weigh between 60–90 lbs. However, both the cutting guides and implants may be manufactured in various sizes, such as small, medium or large, allowing use of the invention in dogs with a range of body weights from approximately 40–120 lbs. In addition, the novel humeral and radioulnar components of the present invention can be altered to successfully articulate with each other independent of component size (e.g., a medium humeral component can articulate with a small radioulnar component).

The design of the present invention overcomes some of the fundamental problems associated with prior implants, including those of Dr. Vasseur's group. The present invention is fundamentally different from any previous human or veterinary total elbow arthroplasty system. The differences include:

1) The implant is unconstrained, not semiconstrained or constrained. This is an important feature which addresses not only the articular surfaces but the motion allowed between components. Unconstrained systems, e.g., most total knee and hip systems, allow motion in more than one plane between components. This makes the ligaments and other periarticular tissues share in much of the mechanical load when the limb is used. The more constrained a system is the more load at the bone-cement and implant-cement interfaces. Increased load bearing leads to a shorter time of failure at the implant-bone, implant-cement, or cement-bone interface. It is believed that constrained systems must go through much more rigorous FDA testing prior to approval when compared to unconstrained systems because of their historical high failure rate. Many human elbow systems are constrained or semiconstrained. The design of the present invention will allow for flexion-extension, supination-pronation, and some cranial-caudal translation.

2) The numeral component is isometric—it can be used in left or right limbs. One advantage of isometry is decreased manufacturing costs. The angle of the stem on the humeral component of the canine implant was determined by morphometric analysis of cadaver dogs. In addition, the radioulnar component of the preferred embodiment of the canine implant has an articular surface that is isometric but the stems and hooks are specific for left and right. This becomes important if the radioulnar component is to be machined as opposed to molded. If machined, manufactures can machine a large number of radioulnar components in which the articular surface is completed but the stems and hooks are left unfinished. The stems and hooks are then finished on an as-needed basis. This saves on inventory costs. Like the humeral stem, the angles of the radioulnar stems were determined by morphometric analysis of cadaver dogs.

3) The implant design incorporates a combination of bone cement and porous ingrowth technologies. The stems that have been tested have been bead blasted for cemented fixation. The surfaces of the stems on the components can be easily altered for porous ingrowth fixation.

The grooves on the sides of the humeral component increase the surface area for increased fixation between the cement and the component. The sizes and shapes of grooves and stems allow for increased cement mantle size without decreasing the strength of the components.

4) The design has only two components. Only two components are needed, keeping the design simple and inexpensive.

5) The surgical technique includes radioulnar synostosis/fusion. The radioulnar component goes into two different bones. These bones normally have a small amount of motion between them which allows for pronation and supination. If a component is placed in both bones and there is motion, the implant will loosen over time. Synostosis or fusion of the two bones in accordance with the present invention protects the implant from this motion and therefore from loosening. The unconstrained nature of the present system will still allow for pronation-supination. The ligaments around the elbow joint and to some degree the implants will be the limiting factor for this motion.

6) No osteotomies need to be surgically repaired to implant the components. Cartilage and its associated bone are removed so the components can be implanted. However, no osteotomies that need surgical repair are needed to get the necessary exposure to put in the components. This decreases costs, surgical time, and patient morbidity.

7) Cutting guides are used for bone removal. The guides ensure that the appropriate amount of bone is removed for each component. This decreases the likelihood of removal of too much bone stock. In addition, the cutting guide for the radioulnar cut incorporates a curved cut of the ulna as opposed to a 90 degree straight cut. A curved cut decreases the likelihood of fracture at this site.

Short-term results with the implants of the present invention show that following surgery the dogs have functional use of the surgery leg with no unexpected complications.

Accordingly, one embodiment of the invention is directed to a two component elbow endoprosthesis comprising a humeral component and a radioulnar component. The humeral component has a condylar portion and a stem portion. The condylar portion is adapted to be received in a resected portion of a distal humerus between the medial and lateral aspects of the humeral condyle. The condylar portion has a proximal end and a distal end. A proximal portion is disposed at the proximal end; an isometric articulating surface, a medial side and a lateral side are disposed at the distal end. The proximal portion has a longitudinal axis and a first cross-sectional area. The articulating surface comprises a arcuate groove disposed circumferentially along the distal end of the condylar portion, midway between the medial side and the lateral side. The humeral stem portion is attached to the proximal end of the proximal portion of the condylar portion. The stem portion is adapted to be received in the medullary canal of the distal humeral shaft. The humeral stem portion has a proximal end and a longitudinal axis which is angled cranially with respect to the longitudinal axis of the proximal portion of the condylar portion so that the condylar portion and stem portion approximate the original angle between the humeral condyle and the humeral shaft. In addition, the stem portion has a second cross sectional area which is smaller than the first cross-sectional area of the proximal portion, thereby forming a shoulder between the humeral stem portion and the proximal portion.

The radioulnar component is a single piece and is designed to articulate with the humeral component. The radioulnar component comprises a head portion comprising an isometric arcuate articulating ridge adapted to articulate with the arcuate groove of the humeral component, a radial stem portion attached to the head portion, which is adapted to be received in the medullary canal of a proximal radial shaft, and an ulnar stem portion attached to the head portion which is adapted to be received in the medullary canal of a proximal ulnar shaft. The radioulnar component may further comprise an ulnar hook attached to the caudal aspect of the head portion for greater implant alignment and stability.

In a preferred embodiment, the humeral stem portion has a rounded proximal end and is angled cranially about 5 degrees. The humeral stem portion may have a plurality of grooves to facilitate affixing it in place with cement. Preferably, these grooves have a reverse wedge profile. Preferably, the entire humeral component is isometric.

Either or both the radial stem portion and ulnar stem portion may be rounded at their distal ends. The radial stem portion is preferably angled medially about 5 degrees from its point of attachment to the head portion. The ulnar stem portion has a longitudinal axis and a medial and a lateral side and is preferably rotated about 30 degrees about the longitudinal axis so that the lateral side is rotated caudally and medially with respect to the head portion. The medial side is rotated cranially and laterally with respect to the head portion. The articular surface (the articulating ridge) of the radioulnar component is isometric.

The proximal portion of the condylar portion may further comprise a plurality of grooves. These grooves may be transverse, longitudinal or both. Preferably, they have a reverse wedge design or profile. The condylar portion may further comprise a pair of ridges disposed on each side of the caudal proximal end of the arcuate groove. The radioulnar component may further comprise two grooves disposed on each side of the articulating ridge.

Another embodiment of the invention is directed to a humeral cutting guide for removing the trochlea of the humerus, in order to prepare the humerus for implantation of an endoprosthetic joint. The cutting guide of this embodiment preferably comprises a proximal portion, a distal portion and a guide bar. The proximal portion has two parallel cutting slots through it. The distal portion has a first face. The proximal portion is affixed to the first face such that the proximal and distal portion are substantially perpendicular to each other. The guide bar is also disposed on the first face of the distal portion so that it is perpendicular to the first face and parallel to the proximal portion.

In a preferred embodiment of this guide, the cutting slots are perpendicular to the distal portion. The humeral cutting guide may further comprise a pilot hole through the distal portion. The pilot hole is adapted to receive a pin disposed in the medullary canal of the distal humerus. The distal portion may further comprise a wedge shaped segment having a plurality of holes adapted for receiving screws to secure the humeral cutting guide to the pin.

Another embodiment of the invention is directed to a radioulnar cutting guide for removing the articular surface of the radius and ulna, in order to prepare these bones for implantation of an endoprosthetic joint. This guide comprises an L-shaped member comprising a first limb and a second limb. The L-shaped member has a cutting surface comprising a first planar surface on the first limb, a second planar surface on the second limb perpendicular to the first planar surface, and a third curved surface disposed between the first and second surfaces. A proximal piece is affixed to the first limb. This proximal piece preferably has a first guide hole adapted for mounting on a pin in the proximal medullary canal of the ulna.

The radioulnar cutting guide may further comprise a second pilot hole through the L-shaped member adapted for receiving a pin placed into the lateral aspect of the ulna to secure the cutting guide. In addition, a cranial piece may be affixed to the second limb, the cranial piece having a pilot hole adapted for receiving a pin placed into the cranial aspect of the radius to secure the cutting guide.

The present invention is also directed to methods for implanting an elbow endoprosthesis in a canine elbow joint. One such method comprises the steps of removing the trochlea of the humerus, removing the articular surface of the ulna and radius and cancellous bone from the proximal medullary canals of the ulna and radius, and, in any order, inserting a radioulnar component into the medullary canals of the radius and ulna and affixing it in place, inserting bone graft between the proximal radius and ulna to encourage rapid synostosis, and inserting a humeral component into the medullary canal of the humerus and affixing it in place.

The humeral and radioulnar components are affixed in place using any suitable material or bone cement, such as PMMA or a bioactive cement.

The trochlea of the humerus is preferably removed using the humeral cutting guide of the present invention. The articular surface of the ulna and radius are preferably removed using the radioulnar cutting guide of the present invention. The elbow endoprosthesis used in this method is preferably the endoprosthesis of the present invention.

In this method, the step of removing the trochlea may comprise the steps of drilling a first hole approximately 10 cm from the trochlear notch of the humerus proximally up the medullary canal, placing a first pin in the first hole until it engages cortical bone, mounting the cutting guide on the first pin, and removing the trochlea of the humerus. The step of removing the articular surface of the radius and ulna and cancellous bone may comprise the steps of placing an ulnar pin retrograde from the mid-ulnar diaphysis through the ulnar shaft exiting at the olecranon, mounting the radioulnar cutting guide on the ulnar pin, removing the articular surface of the ulna and radius, and removing cancellous bone to a depth of about 1 cm from the medullary canal of the ulna and radius.

In a preferred embodiment of the method, the radioulnar component is installed first, and the step of inserting and affixing the humeral component comprises positioning a humeral component in the distal humeral shaft, reducing the radius and ulna, allowing articulation between the humeral and radioulnar components, flexing and extending the joint, allowing the humeral and radioulnar components to find a neutral position, and allowing the cement in the medullary canal of the humerus to harden.

Still another embodiment is directed to a method for implanting an elbow endoprosthesis in a canine elbow joint, comprising the steps of drilling a first hole approximately 10 cm from the trochlear notch of the humerus proximally up the medullary canal, placing a first pin in the first hole until it engages cortical bone, mounting a cutting guide on the first pin, removing the trochlea of the humerus, removing the cutting guide, placing a second pin retrograde from the midulnar diaphysis through the ulnar shaft exiting at the olecranon, mounting a radioulnar cutting guide on the second pin, removing the articular surface of the ulna and radius, removing cancellous bone to a depth of about 1 cm from the medullary canal of the ulna and radius, placing a cement, such as PMMA, into the medullary canals of the radius and ulna, inserting a radioulnar component and holding it in place until the cement hardens, inserting bone graft between the proximal radius and ulna to encourage rapid synostosis, placing cement into the medullary canal of the humeral shaft, positioning a humeral component in the distal humeral shaft, reducing the radius and ulna, allowing articulation between the humeral and radioulnar components, flexing and extending the joint, allowing the humeral and radioulnar components to find a neutral position, and allowing the cement in the medullary canal of the humerus to harden.

The following experiments are offered to illustrate embodiments of the invention and should not be viewed as limiting the scope of the invention.

EXAMPLE 1

Implant Design

Morphometric analysis of the canine elbow was performed using computed tomographic, radiographic and hand-measured data. Twelve pairs of humerus', radius' and ulnas were collected from Labrador Retriever or Rottweiler dogs aged 2 to 8 years of age. All dogs had died or been euthanized from causes unrelated to lameness. Computed tomography and radiography were performed on bones to ensure maturity, lack of skeletal abnormalities and lack of elbow osteoarthritis. Soft tissues were removed, and measurements were performed describing the morphology of the elbow joint. Morphometric data was used in conjunction with relevant peer reviewed literature to develop total elbow arthroplasty implants, cutting guides that would reliably cut the bones (humerus, radius, and ulna) for implantation of the implants, and a surgical technique that could be safely and reliably performed.

Descriptive mechanical evaluation (range of motion freely allowed) between the implants was performed. The amount of flexion to extension, mediolateral and craniocaudal translation, and pronation and supination allowed was noted and found to be similar to previously published data.

EXAMPLE 2

Implantation of Endoprosthetic Joint

Dogs were evaluated by physical exam, radiography, computed tomography, and computed assisted force plate gait analysis before surgery. Dogs were placed under general anesthesia. Intravenous antibiotics, sodium cephalexin (Eli Lilly & Co.) (25 mg/kg), were administered following intubation and every 2 hours until anesthetic recovery was complete. The dogs were placed in lateral recumbency and a standard aseptic preparation of the forelimb was performed. A lateral approach to the head of the radius and lateral compartments of the elbow joint was slightly modified by incision and retraction of the lateral digital extensor muscle. (Johnson J A, Austin C, Breur G J. Incidence of canine appendicular musculoskeletal disorders in 16 veterinary teaching hospitals from 1980 through 1989. V.C.O.T. 7:56–69;1994.) (Morrey, B F, Adams R A. Semiconstrained elbow replacement for distal humeral nonunion. J Bone Joint Surg [Br] 77-B:67–72;1995.) (Piermattei D L, Greeley R G. An atlas of surgical approaches to the bones of the dog and cat. (ed 2) Philadelphia, W. B. Saunders, 96–7, 1979.) The radius and ulna were luxated laterally exposing the humeral condyle and the articular surface of all three bones.

Referring to FIGS. 7–12, the humerus was prepared for implantation of the humeral component using the specially designed humeral cutting guide 37 of the present invention. A drill bit (5 to 9 mm) was used to drill a first hole into the humeral medullary canal approximately 5 cm, from distal to proximal, starting at the middle and dorsal aspect of the trochlear notch. The drill hole ran approximately 10 cm from the dorsal aspect of the trochlear notch of the humerus proximally up the medullary canal. The identical drill bit was used to drill a hole perpendicular to the long axis of the humeral shaft into the trochlear notch. A ¼" pin or intramedullary nail 36 was placed in the first hole in the humeral medullary canal, following the direction of the drill hole, and was advanced up the shaft of the humerus, until it engaged cortical bone. Humeral cutting guide 37 was mounted onto the humerus by sliding guide 37 onto nail 36. Cutting guide slots 41a and 41b were then aligned evenly on either side of the condyle 32 to match the medial and lateral extremes of the cranial aspect of the humeral articular cartilage, and guide 37 was temporarily nailed into place. Humeral cutting guide 37 was secured in place by drilling a pin through pilot hole 40 in cutting guide 37 and into the humeral condyle. This prevented rotation of the cutting guide. Screws 39 in cutting guide 37 were tightened to further secure cutting guide 37.

The trochlea/articular cartilage of the humeral condyle was removed by using a saw such as a power driven saw (e.g., minidriver; 3M©) through cutting guide slots 41a and 41b. The bone cut was made with the saw blade placed through the cutting slots 41a and 41b located on cutting guide 37. Cutting guide 37 was then removed. The cut ends were made smooth using a flat bone file. Care was taken not to remove more bone stock than necessary.

Radioulnar component 2 was implanted as follows. A hole, approximately 5 cm below the level of the radial head, was drilled using a 2.0 mm drill bit from the caudal aspect of the ulna through the radius. A glide hole (2.7 mm) was drilled through the ulna 3–4 cm below the level of the ulnar coronoid. The hole was measured and tapped for a 2.7 mm screw. The screw was not inserted at this time. This hole was preplaced to allow for relatively normal placement of the screw at a later time. A 1 cm length ulna ostectomy was performed approximately 3–4 cm below the level of the ulnar screw hole. This bone was saved for later use as cancellous autograft. An ⅛" pin was placed in retrograde fashion from the ulnar ostectomy site up and through the ulnar shaft exiting at the olecranon.

Referring now to FIGS. 13–15, radioulnar cutting guide 78 was mounted to pin 77. The cranial aspect of the guide was placed just below the level of the articular surface of the radial head and the guide was temporarily pinned into place using pins placed through lateral pilot hole 79 and cranial pilot hole 80 on the guide. The articular surface of the ulna and radius was removed using a power driven saw placed along cutting surface 81 provided by the radioulnar cutting guide 78. The radial and ulnar shaft were prepared for the component by drilling their respective shafts with a drill bit to a depth of approximately 4 cm. The cancellous bone was removed (to a depth of about 1 cm) from the ulna and radius. A 2.7 mm screw was positioned into the preplaced hole between the radius and ulna. The bone was flushed. A trial component was placed into the radius and ulna to check for fit. Polymethylmethacrylate (PMMA) was prepared and placed into the ulnar and radial medullary canals. The radioulnar component 2 was manually positioned by alignment of the implant edges with the cut edges of the bones and held in place until the PMMA hardened. Bone graft was placed between the proximal radius and ulna to encourage rapid synostosis.

The humerus was flushed and suctioned. A trial humeral component 1 was placed into the prepared humerus to confirm fit and then removed. The stem 11 of the component should slide freely into the humeral canal. The humeral component 1 was manually positioned and aligned so the shoulder 9 of the implant rested against the distal aspect of the humeral shaft. The curved, polished articular surface of the component followed the curvature of and protruded just distal to the cut bone of the humeral condyle. PMMA was prepared and placed into the humeral medullary canal and adjacent to the cut surface of the humerus. The humeral component was implanted. Prior to hardening of the PMMA in the humerus, the radius and ulna were reduced into a normal position allowing articulation between the implants. The joint was placed through a range of flexion and extension; this allowed the components to find a neutral position thus reducing post fixation binding between the implants.

Although the humeral and radioulnar components of the preferred embodiment were secured using bone cement, in an alternate embodiment the components may be further secured using screws. For example, a 2.7 mm diameter screw (approximately 16–20 mm in length) may be positioned from a preplaced glide hole in the lateral aspect of the condyle into the humeral implant and again from the medial side. This causes compression between the lateral and medial aspects of the humeral condyle and the implant.

The joint was flushed and closed in a routine fashion, with special attention given to reconstruction of the insertion of the lateral collateral ligament which was avulsed from the radius. Postoperative radiography was performed during the immediate postoperative period.

Exercise was limited in all dogs for the first 8 weeks of the treatment period. Orthopedic, radiographic and computed tomographic evaluation and force plate gait analysis was performed in dogs every 12 weeks for 48 weeks. Success was determined by comparing postoperative to preoperative results.

EXAMPLE 3

In vivo study

In an initial study of the effect of total elbow arthroplasty in normal dogs, 2 of 6 dogs had good results 6 months after surgery. These 2 dogs had a mean peak vertical force (PVF) 82% of presurgical normal. Normal dogs have a PVF 70–75% of normal 6 months after femoral head and neck excision and 95% of normal 6 months after total hip replacement. The purpose of this study was to test the effect of a modified total elbow arthroplasty system in normal dogs.

A second study was performed using six different dogs. The humeral component used in these six dogs was made of stainless steel and a radioulnar component from UHMWPE. The articulation was unconstrained. Before surgery orthopedic, radiographic and kinetic (force-plate gait analysis) exams were performed in order to determine that the dog was normal and to establish presurgical guidelines. A modified lateral approach to the elbow joint was made and the elbow was luxated laterally. Bone on the humerus, radius, and ulna with articular cartilage was removed using cutting guides. The bones were prepared for the implants using drill bits and a bone file. The implants were secured in place with bone cement. A distal ulnar ostectomy was performed and the bone used as graft between the proximal aspect of the radius and ulna to encourage radioulnar synostosis. Routine closure was performed and postoperative radiographs taken. Exercise was restricted for the first 2 weeks after surgery; the dogs were then given 15 minute leash walks twice daily. Ten weeks after surgery orthopedic, radiographic and kinetic exams were repeated. The dogs were evaluated every 10–12 weeks after surgery and maintained for a minimum of 6 months.

Postoperative orthopedic exam found dogs to have 110 degrees of pain free range of motion. Surprisingly, motion was most restricted in flexion and extension was normal. Radiographic findings were unremarkable with the exception of osteomyelitis being present in one dog. At four months after surgery, kinetic examination determined mean PVF to be 75% of presurgical normal with a range from 45% to 92% of normal. The dog with a PVF 45% of normal was the dog with osteomyelitis. Lameness continued to resolve in each dog.

Other embodiments and uses of the invention will be apparent to those skilled in the art from consideration of the specification and practice of the invention disclosed herein. Although the invention has been described in connection with the canine elbow, it can be easily adapted for use in other species, including other quadrupeds and man. The specification and examples should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

What is claimed is:

1. A two component elbow endoprosthesis comprising:
   a humeral component, the humeral component comprising:
   (i) a condylar portion adapted to be received in a resected portion of a distal humerus between the medial and lateral aspects of the humeral condyle, the condylar portion having a proximal end and a distal end and comprising a proximal portion disposed at the proximal end and an isometric articulating surface, a medial side and a lateral side disposed at the distal end, the proximal portion having a longitudinal axis and a first cross-sectional area, the articulating surface comprising an arcuate groove disposed circumferentially along the distal end of the condylar portion, midway between the medial side and the lateral side, and
   (ii) a humeral stem portion attached to the proximal portion of the condylar portion, the humeral stem adapted to be received in the medullary canal of the distal humeral shaft, the humeral stem portion having a proximal end and a longitudinal axis angled cranially with respect to the longitudinal axis of the proximal portion, the stem portion having a second cross sectional area smaller than the first cross-sectional area of the proximal portion, thereby forming a shoulder between the humeral stem portion and the proximal portion; and
   a radioulnar component for articulating with the humeral component, the radioulnar component comprising:
   (i) a head portion comprising an isometric arcuate articulating ridge adapted to articulate with the arcuate groove of the humeral component,
   (ii) a radial stem portion attached to the head portion adapted to be received in the medullary canal of a proximal radial shaft, and
   (iii) an ulnar stem portion attached to the head portion adapted to be received in the medullary canal of a proximal ulnar shaft.

2. The endoprosthesis of claim 1 wherein the humeral stem portion further comprises a rounded proximal end.

3. The endoprosthesis of claim 1 wherein the humeral stem portion is angled cranially about 5 degrees.

4. The endoprosthesis of claim 1 wherein the humeral component is isometric.

5. The endoprosthesis of claim 1 wherein the humeral stem portion further comprises a plurality of grooves.

6. The endoprosthesis of claim 1 wherein the radial stem portion is angled medially 5 degrees from the point of attachment of the radial stem portion to the head portion.

7. The endoprosthesis of claim 1 wherein the ulnar stem portion has a longitudinal axis and a lateral side, and is affixed to the head portion in a position wherein the stem is rotated about 30 degrees about the longitudinal axis so that the lateral side is rotated caudally and medially with respect to the head portion.

8. The endoprosthesis of claim 1 wherein the radioulnar component further comprises an ulnar wedge attached to the caudal aspect of the head portion.

9. The endoprosthesis of claim 1 wherein the radial stem portion and ulnar stem portion are rounded at their distal ends.

10. The endoprosthesis of claim 1 wherein the proximal portion of the condylar portion further comprises a plurality of grooves.

11. The endoprosthesis of claim 1 wherein the condylar portion further comprises a pair of ridges disposed on each side of the caudal proximal end of the arcuate groove.

12. The endoprosthesis of claim 1 wherein the radioulnar component further comprises two grooves disposed on each side of the articulating ridge.

13. The endoprosthesis of claim 1 wherein the endoprosthesis is designed to replace a canine elbow.

14. A method for implanting an elbow endoprosthesis in an elbow joint, comprising the steps of:
   removing the trochlea of the humerus;
   removing the articular surface of the ulna and radius and cancellous bone from the proximal medullary canals of the ulna and radius, and, in any order,
   inserting a radioulnar component into the medullary canals of the radius and ulna and affixing the radioulnar component in place;
   inserting bone graft between the proximal radius and ulna to encourage rapid synostosis; and
   inserting a humeral component into the medullary canal of the humerus and affixing the humeral component in place, and wherein the elbow endoprosthesis comprises:
   a humeral component, the humeral component comprising:
   (i) a condylar portion adapted to be received in a resected portion of a distal humerus between the medial and lateral aspects of the humeral condyle, the condylar portion having a proximal end and a distal end and comprising a proximal portion disposed at the proximal end and an isometric articulating surface, a medial side and a lateral side disposed at the distal end, the proximal portion having a longitudinal axis and a first cross-sectional area, the articulating surface comprising an arcuate groove disposed circumferentially along the distal end of the condylar portion, midway between the medial side and the lateral side, and
   (ii) a humeral stem portion attached to the proximal portion of the condylar portion, the humeral stem adapted to be received in the medullary canal of the distal humeral shaft, the humeral stem portion having a proximal end and a longitudinal axis angled cranially with respect to the longitudinal axis of the proximal portion, the stem portion having a second cross sectional area smaller than the first cross-sectional area of the proximal portion, thereby forming a shoulder between the humeral stem portion and the proximal portion; and
   a radioulnar component for articulating with the humeral component, the radioulnar component comprising:
   (i) ahead portion comprising an isometric arcuate articulating ridge adapted to articulate with the arcuate groove of the humeral component,
   (ii) a radial stem portion attached to the head portion adapted to be received in the medullary canal of a proximal radial shaft, and
   (iii) an ulnar stem portion attached to the head portion adapted to be received in the medullary canal of a proximal ulnar shaft.

* * * * *